United States Patent
Mirsepassi et al.

(10) Patent No.: US 10,295,718 B2
(45) Date of Patent: May 21, 2019

(54) DIVERGING LIGHT FROM FIBER OPTICS ILLUMINATION DELIVERY SYSTEMS

(71) Applicant: Novartis AG, Basel (CH)

(72) Inventors: Alireza Mirsepassi, Irvine, CA (US);
Ronald T. Smith, Irvine, CA (US);
Michael J. Papac, North Tustin, CA (US); Chenguang Diao, Irvine, CA (US)

(73) Assignee: Novaris AG, Basel (CH)

( * ) Notice: Subject to any disclaimer, the term of this patent is extended or adjusted under 35 U.S.C. 154(b) by 562 days.

(21) Appl. No.: 14/973,939

(22) Filed: Dec. 18, 2015

(65) Prior Publication Data

US 2017/0176660 A1    Jun. 22, 2017

(51) Int. Cl.
| | | |
|---|---|---|
| G02B 6/26 | (2006.01) | |
| F21V 8/00 | (2006.01) | |
| G02B 5/02 | (2006.01) | |
| A61B 1/07 | (2006.01) | |
| A61F 9/008 | (2006.01) | |
| G02B 6/24 | (2006.01) | |
| A61B 90/00 | (2016.01) | |
| A61F 9/007 | (2006.01) | |

(52) U.S. Cl.
CPC .............. *G02B 6/0008* (2013.01); *A61B 1/07* (2013.01); *A61B 90/36* (2016.02); *A61F 9/008* (2013.01); *A61F 9/00736* (2013.01); *G02B 5/021* (2013.01); *G02B 5/0242* (2013.01); *G02B 5/0247* (2013.01); *G02B 6/241* (2013.01); *G02B 6/262* (2013.01)

(58) Field of Classification Search
CPC ....... G02B 6/0008; G02B 6/262; G02B 6/241
See application file for complete search history.

(56) References Cited

U.S. PATENT DOCUMENTS

| | | | |
|---|---|---|---|
| 2002/0028041 A1 | 3/2002 | Easley | |
| 2002/0054735 A1 | 5/2002 | Bernard | |
| 2003/0128944 A1 | 7/2003 | Skutnik | |
| 2005/0075628 A1 | 4/2005 | Cazzini | |
| 2005/0105877 A1* | 5/2005 | Nappi | G02B 6/262 |
| | | | 385/140 |
| 2006/0018596 A1* | 1/2006 | Loebel | A61B 18/22 |
| | | | 385/38 |
| 2009/0210038 A1 | 8/2009 | Neuberger | |
| 2014/0270639 A1* | 9/2014 | James, III | C03C 3/089 |
| | | | 385/31 |

FOREIGN PATENT DOCUMENTS

| | | |
|---|---|---|
| EP | 1850727 B1 | 11/2007 |
| GB | 2175682 A1 | 12/1986 |
| WO | 2014/165048 | 10/2014 |

* cited by examiner

*Primary Examiner* — Andrew J Coughlin

(57) ABSTRACT

An illumination fiber optics is provided that includes an optical fiber, configured to receive illumination light at a proximal end from a light source; and a light-scattering element, at a distal end of the optical fiber, configured to receive the illumination light from the optical fiber at a proximal end and to emit the illumination light at a distal end in a wide angle. The illumination fiber optics can be prepared by providing an optical fiber, configured to receive illumination light at a proximal end from a light source; and creating a light-scattering element at a distal end of the optical fiber, configured to receive the illumination light from the optical fiber at a proximal end and to emit the illumination light at a distal end in a wide angle.

16 Claims, 23 Drawing Sheets

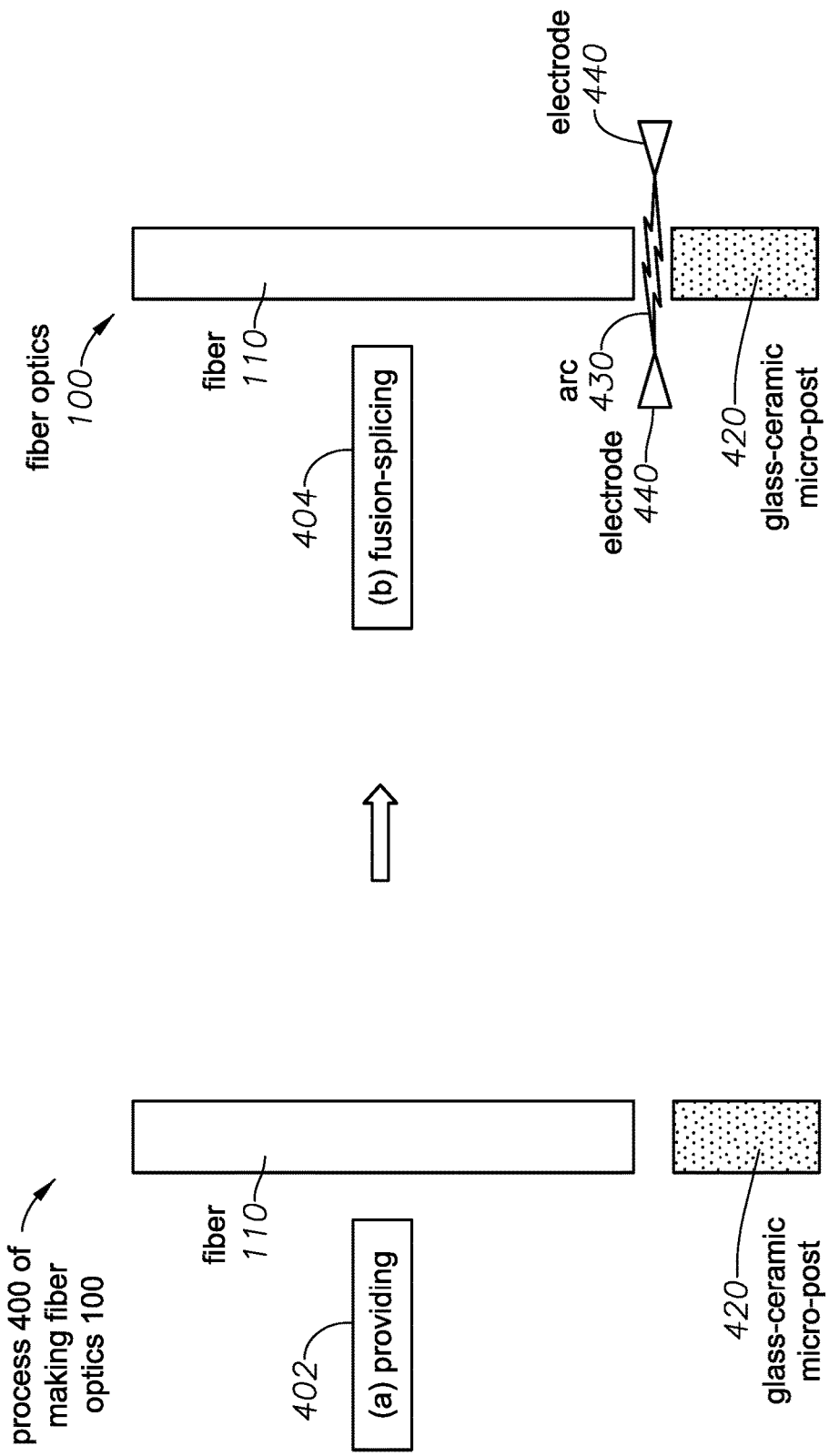

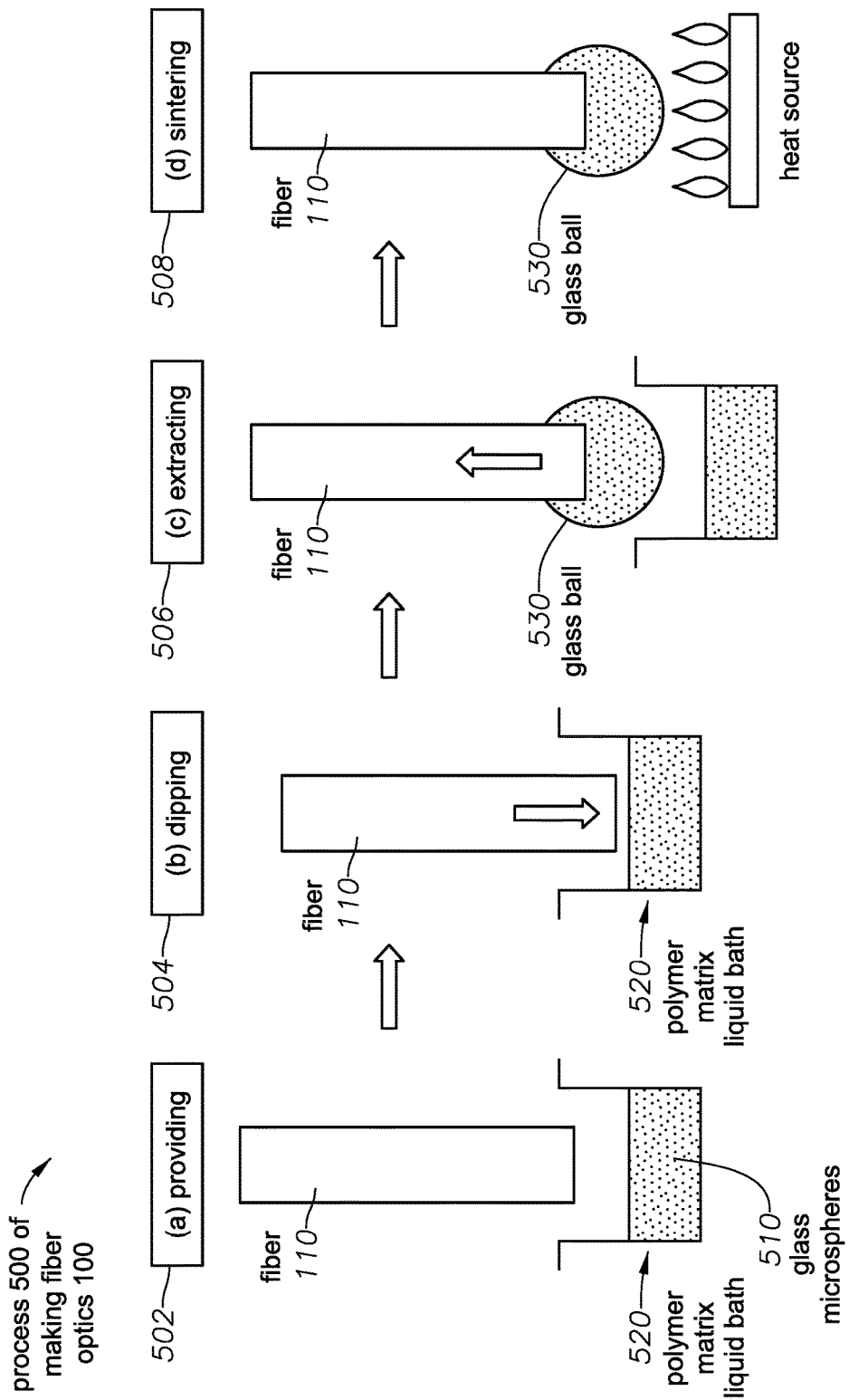

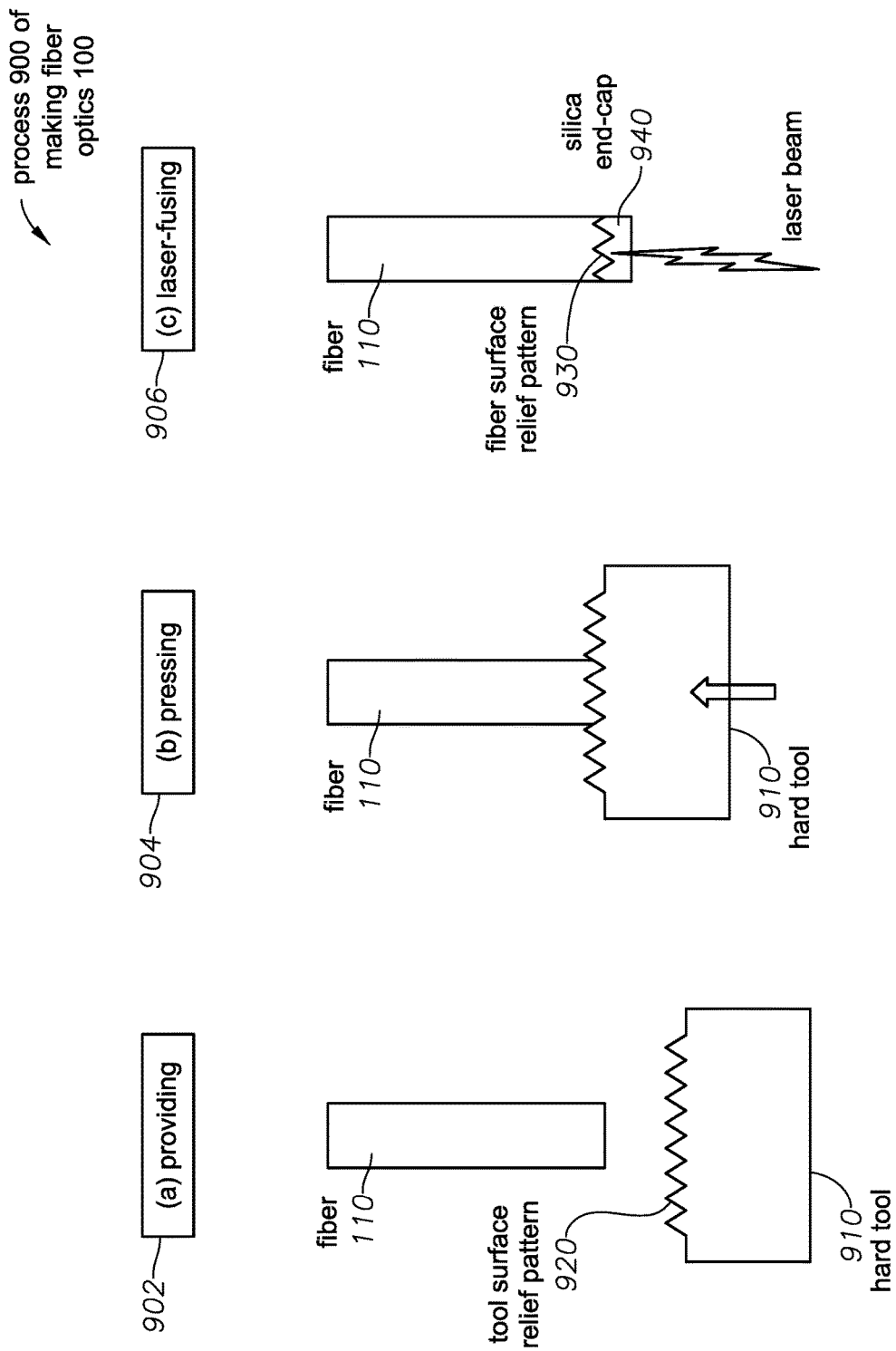

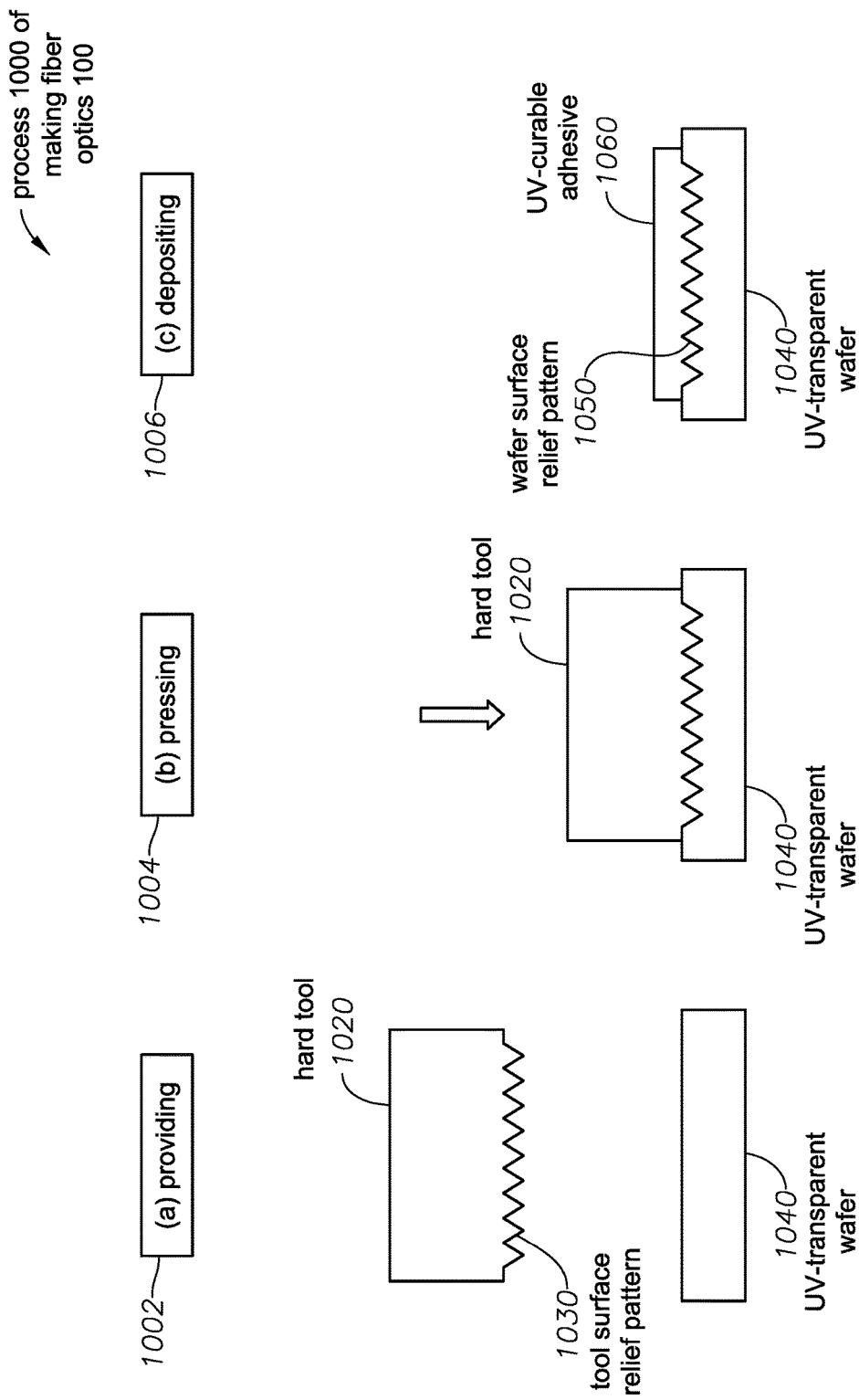

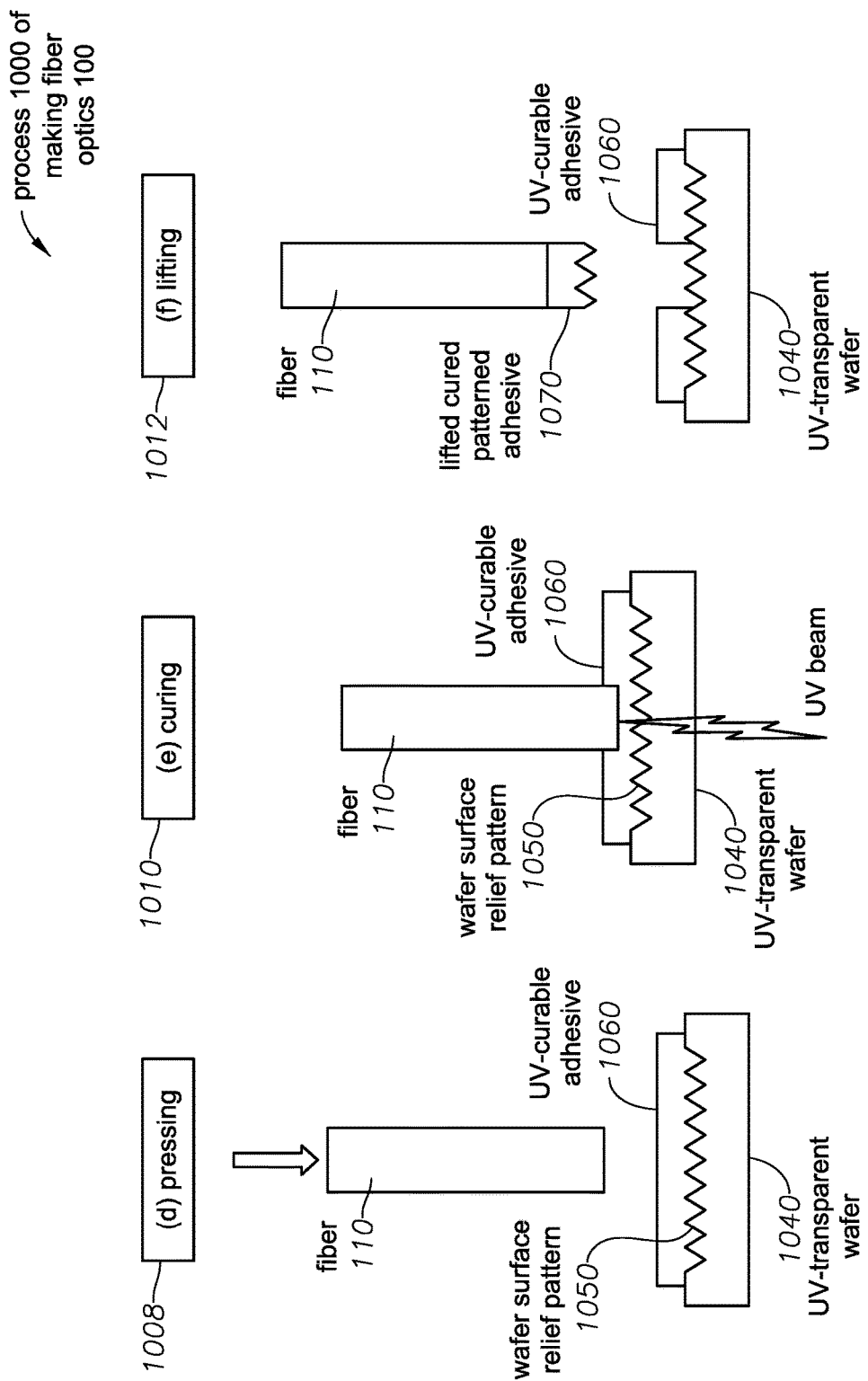

DIVERGING LIGHT FROM FIBER OPTICS ILLUMINATION DELIVERY SYSTEMS

TECHNICAL FIELD

This patent document is related to fiber optics illuminators. In more detail, this patent document is related to thin fiber optics illuminators with a wide light emission angle.

BACKGROUND

During ophthalmic surgery in the posterior region, such as during vitreo-retinal surgical procedures, illuminating the surgical region is a high priority. The illuminators need to have a small diameter so that a small incision is sufficient for their insertion. At the same time, they need to emit the illumination light in as wide an angle as possible to illuminate the largest possible area. The angle of emission is controlled by the numerical aperture and thus the diameter of the fibers. In general, achieving wider emission angles necessitates thicker fibers. These two design criteria of small fiber diameters and large illumination angles are therefore in direct competition with each other, making achieving a good design optimum a genuine challenge.

Some existing illuminators increase the illumination angle by tapering the optical fiber to a smaller diameter towards the tip. Analyzing the light rays shows that such fiber optic illuminators can emit the light rays with larger angles compared to the angles the numerical aperture of the fiber would naturally support. The tapering of the fibers is typically performed thermally, mechanically, or chemically.

However, the performance of these tapered fiber illuminators turns out to be quite sensitive to manufacturing the fibers with precisely the right taper angle. Adhering to this low tolerance is a substantial manufacturing challenge. Further, achieving the higher angular divergence also poses tight design requirements on the refractive index of the fiber core and the cladding.

Other illuminators are fabricated by modifying the tip of the optical fiber by mechanical, irradiative or chemical processes. However, to preserve the integrity of the fibers during these often forceful fabrication steps, these fibers typically have to be encased in a manufacturing sheath, or jacket, for support. This requirement typically complicates the manufacturing and makes it more expensive.

Further, in today's surgical practice, the surgeon typically holds a phaco-tip in one hand and a vitreous cutter in the other, both entered into the eye via dedicated incisions. Therefore, an additional, highly trained nurse or junior medical professional is needed to hold the illuminator, inserted through a third incision. If the illuminator could be integrated with one of the other surgical devices, that could eliminate the need for a third hand, making the surgical procedure two-handed, or bi-manual, performable by the surgeon alone. Reducing the number of surgical professionals needed for these ophthalmic procedures would have numerous advantages.

Also, needing fewer incisions would reduce the deformation and structural weakening of the eye caused by the incisions of the ophthalmic surgery.

With today's illuminators it is not easy to satisfy the above needs, as they often use fibers that are thicker, such as having a fiber diameter in excess of 500 microns. Moreover, they often have a jacket, or sheath, for strength. If such a thick illuminator were somehow affixed to one of the other surgical devices, that would increase the diameter, or form factor, of that integrated device substantially, thus increasing the size of the incision necessary for its insertion, to undesirable levels.

Therefore, there is a need for illuminators that have small diameters, yet can emit illuminating light into a wide angle; do not require a sheath or jacket for their manufacture; and can be integrated with another surgical device without increasing the form factor of the device, thus also reducing the number of incisions necessary for the ophthalmic surgical procedure, as well as the number of hands and thus the number of professionals needed for ophthalmic surgery.

SUMMARY

Embodiments in this patent document address the above challenges by introducing an illumination fiber optics, comprising: an optical fiber, configured to receive illumination light at a proximal end from a light source; and a light-scattering element, at a distal end of the optical fiber, configured to receive the illumination light from the optical fiber at a proximal end and to emit the illumination light at a distal end in a wide angle.

In some embodiments, an illumination fiber optics for an ophthalmic device is prepared by a process comprising the steps of: providing an optical fiber, configured to receive illumination light at a proximal end from a light source; and creating a light-scattering element at a distal end of the optical fiber, configured to receive the illumination light from the optical fiber at a proximal end and to emit the illumination light at a distal end in a wide angle.

In some embodiments, a process can comprise the steps of: providing a micro-post comprising a glass-ceramic light-scattering element that includes at least one of a ceramic, a glass ceramic, an immiscible glass, a porous glass, opal glass, amorphous glass, an aerated glass, and a nanostructured glass; and fusion-splicing the glass-ceramic micro-post to the optical fiber by pulling an arc between electrodes across a gap formed by the optical fiber and the glass-ceramic micro-post; maintaining the arc for a time sufficiently long to make facing surfaces of the optical fiber and the micro-post one of malleable and molten; and pushing and thereby fusing together the facing surfaces of the optical fiber and the micro-post. Some embodiments can include fusing the glass-ceramic micro-post to the optical fiber by applying a laser beam to heat up at least one of the facing surfaces of the optical fiber and the glass-ceramic micro-post.

BRIEF DESCRIPTION OF THE DRAWINGS

FIGS. 7A-D illustrate processes 400/450 of making the fiber optics 100.

FIGS. 9A-D illustrate a process 500 of making the fiber optics 100.

FIGS. 17A-D illustrate a process 900 of making the fiber optics 100.

FIGS. 19A-F illustrate a process 1000 of making the fiber optics 100.

DETAILED DESCRIPTION

Embodiments described herein address the above needs and challenges by introducing the following advantageous aspects.

(a) In embodiments, the fiber optics is fabricated using an unusually small diameter optical fiber. Instead of tapering the fiber, a light-scattering element is formed at the distal end of the optical fiber.

(b) With the fabrication processes described herein, no jacket or sheath is required to support the individual fiber optics, not even for its manufacturing process. This makes the fabrication simpler and therefore cheaper.

(c) The small diameter of the fiber optics and the lack of a jacket or sheath makes it also possible to integrate the fiber optics with a wide variety of surgical devices to provide illumination for the surgical procedure without increasing the device's form factor, or effective diameter. Such "self-illuminating" surgical devices eliminate the need to cut the presently customary separate third incision for the surgical illumination source. Fewer incisions advantageously reduce the deformation and structural weakening of the eye caused by the ophthalmic surgery.

(d) These self-illuminating devices also reduce the number of hands required to hold the surgical instruments. Surgeries that normally require three hands and thus a highly trained nurse or junior doctor next to the lead surgeon to hold all the implements, can be transformed from a three-hand procedure to a two-hands, or bi-manual, procedure by the here-described self-illuminating surgical devices. This means that the need for the second surgical staff member can be advantageously eliminated by using the here-described devices.

(e) The here-presented designs and processes reduce the sensitivity to the precision of the fiber fabrication, such as the critical sensitivity of the presently widely used tapering of the fiber, since the here-presented designs form a separate light-scattering element at the distal end of the fiber. In general, less sensitive designs reduce costs and increase yields.

Figure 1:
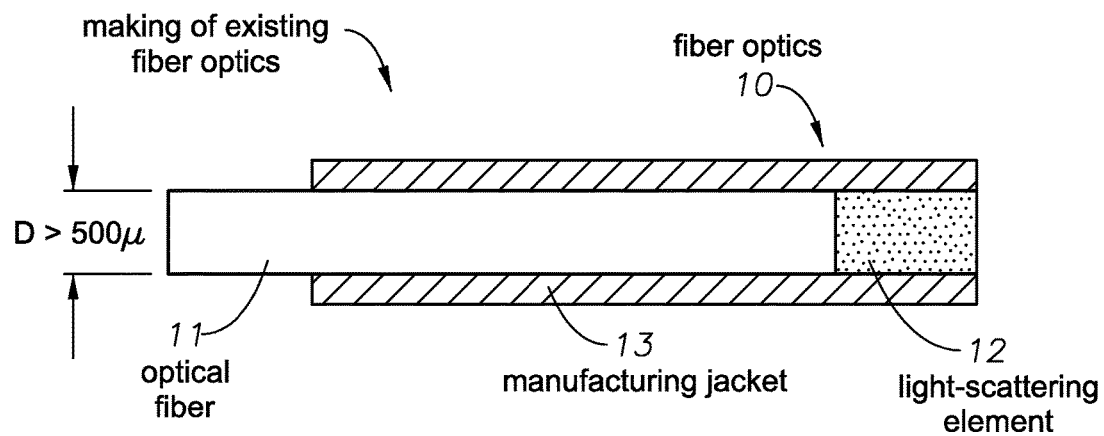
FIG. 1 illustrates a process of making existing fiber optics.

FIG. 1 illustrates a process of making existing fiber optics with presently accepted procedures. The fiber optics 10 can include an optical fiber 11 and a light-scattering element 12 at its distal end. Typically, the individual fiber optics 10 is supported by a jacket 13, or sheath, to provide stability and structural strength for the fiber optics 10. This jacket is especially useful for the fabrication process, as the formation of the light-scattering element 12 with mechanical or chemical means, or with the application of high-power lasers can de-stabilize, crack or even disintegrate the fiber 11.

The facts that existing fiber optics 10 often have a diameter in excess of 500 microns, and that they require a jacket, at least for the fabrication, makes these existing fiber optics 10 thick, with a substantial outer diameter ("OD"). Therefore, attaching them to a surgical device would increase the form factor, or effective diameter, of this surgical device. This would require cutting an undesirably larger incision. Therefore, reducing the diameter of the illumination fiber optics is a high-priority need for surgical applications.

Figure 2:
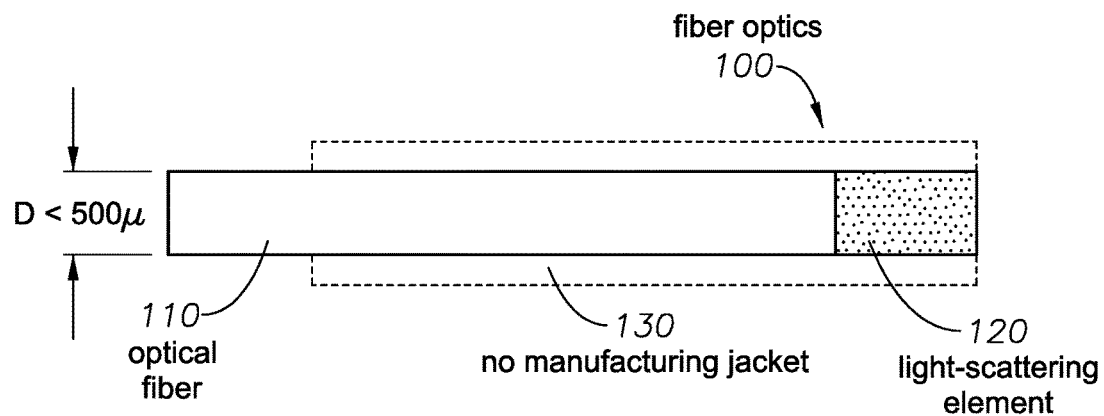
FIG. 2 illustrates a process of making embodiments of fiber optics 100.

FIG. 2 shows embodiments of an illumination fiber optics 100 that has a substantially smaller diameter than existing systems. Fiber optics 100 can include a an optical fiber 110, or simply fiber 110, configured to receive illumination light at a proximal end from a light source, and a light-scattering element 120, formed at a distal end of the fiber 110. The light-scattering element 120 can be formed separately and then affixed to the optical fiber 110. In other embodiments, the light-scattering element 120 can be formed directly at, on, or in the distal end of the fiber 110. The light-scattering element 120 can be configured to receive the illumination light from the fiber 110 at its proximal end and to emit the illumination light at its distal end in a wide angle.

The outer diameter D of the fiber optics 100 can be less than 500 microns. In some embodiments, the outer diameter D can be less than 150 microns. In yet other embodiments, the outer diameter D can be less than 50 microns.

In some embodiments, the fiber optics 100 can be tapered: it can have an outer diameter less than 50 microns at a distal end, and an outer diameter greater than 50 microns at a proximal end.

In some embodiments, a proximal diameter of the light-scattering element 120 can less, equal or greater than a distal diameter of the optical fiber 110.

Finally, when the fiber optics 100 is fabricated with the here-described processes, the optical fiber 110 and the light-scattering element 120 can be manufactured without using a manufacturing jacket 130.

Figure 3A:
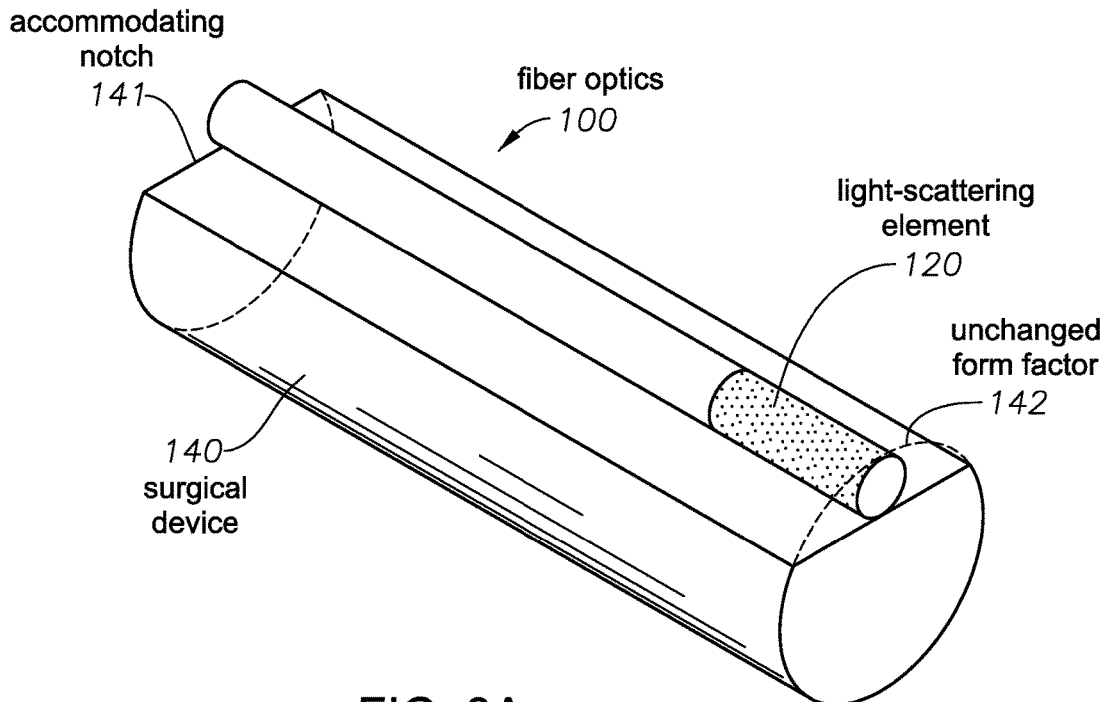
FIGS. 3A-B illustrate a fiber optics 100 and a surgical device.
Figure 3B:
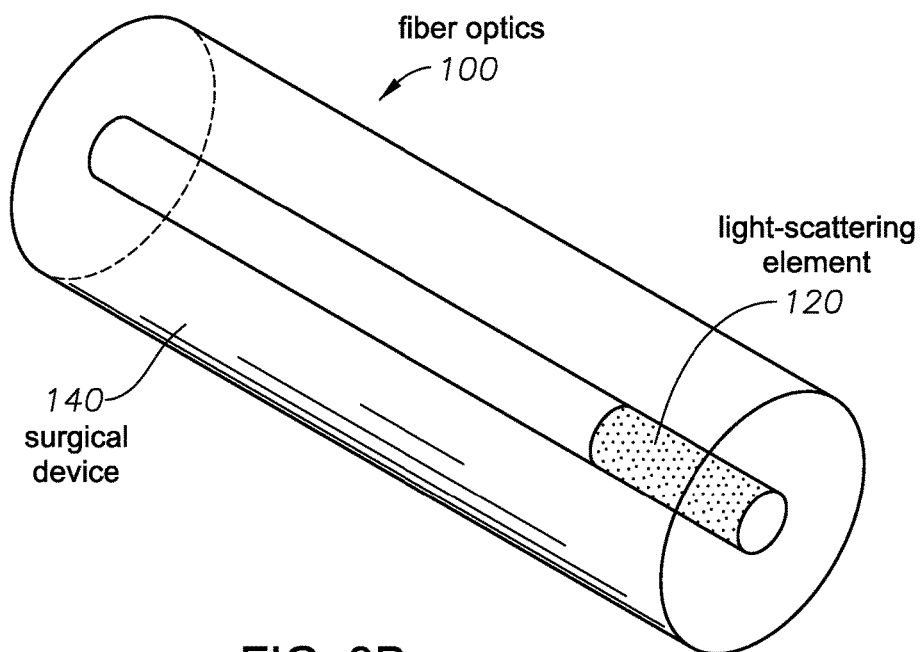

FIGS. 3A-B illustrate that embodiments of these small-diameter fiber optics 100 can be attached to an ophthalmic surgical device 140. In FIG. 3A, the ophthalmic surgical device 140 can have an accommodating notch 141 formed on a side and the fiber optics 100 can be attached to the surgical device 140 along this notch 141, in an aligned manner. With the formation of the accommodating notch 141, the unusually small fiber diameter and the lack of a jacket for the fiber optics 100, attaching the fiber optics 100 to the surgical device 140 has the ability not to increase the overall form factor, cross section, or outer diameter 142 of the surgical device 140. For example, an ophthalmic surgical device 140 having an outer diameter thinner than 23 gauge (i.e. having a larger gauge) can retain its gauge even after the attachment of the fiber optics 100 to its accommodating notch 141.

The fiber optics 100 can be configured to emit the illumination light at the distal end of the light-scattering element 120 to serve as an illumination light for a surgical procedure performed by the surgical device 140.

FIG. 3B illustrates another possible embodiment, when the fiber optics 100 is not attached to the surgical device 140. Instead, it is centrally embedded in the ophthalmic surgical device 140 along its optical axis. Such implementations can have extremely small form factors, or outer diameters, in some cases thinner than 40 gauge.

The fiber optics 100 can be combined with a wide array of ophthalmic surgical devices 140, including an articulated laser probe, an illuminating chandelier, a trocar cannula, a balanced salt solution (BSS) infusion line, a nanofiber endo-illuminator, a forceps, a phaco-surgical device, a retinal-surgical device, or a vitreous-cutter.

In some embodiments of the fiber optics 100, the wide angle of the light emission by the light-scattering element 120 can be characterized by the illumination intensity in air at 60 degrees off an optical axis of the fiber optics 100 being greater than 2% of the illumination intensity in air at 0 degrees, along the optical axis of the fiber optics 100.

In other embodiments, the wide angle emission can be characterized by the illumination intensity in air at 30 degrees off an optical axis of the fiber optics 100 being greater than 50% of the illumination intensity in air at 0 degrees, along the optical axis of the fiber optics 100.

Figure 4:
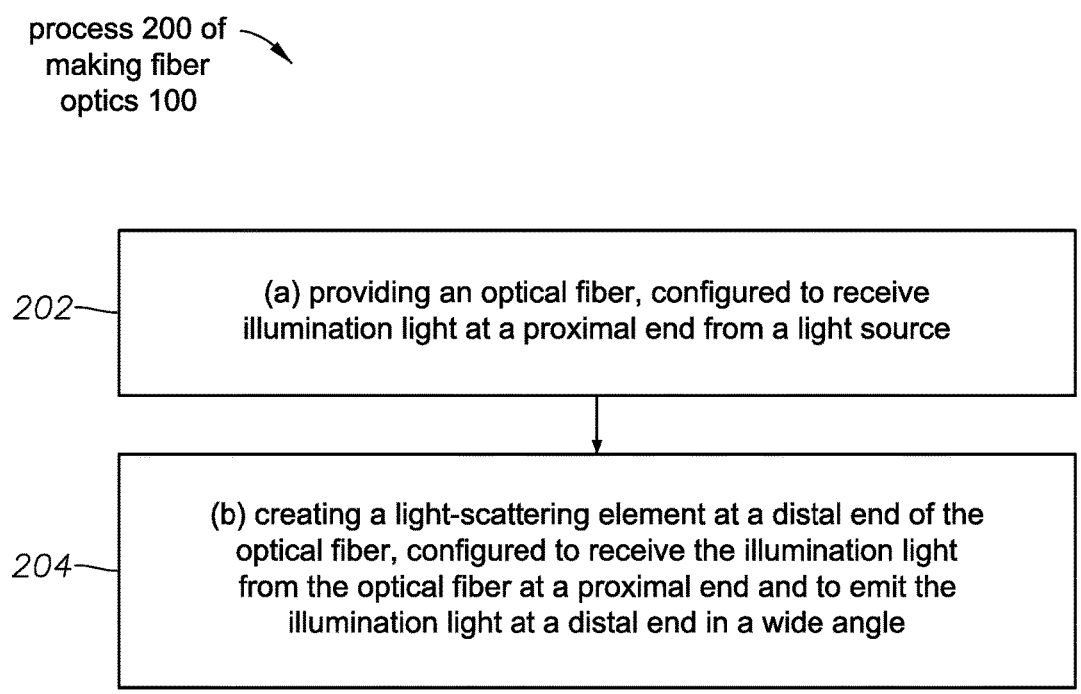
FIG. 4 illustrates a process 200 of making the fiber optics 100.
Figure 5:
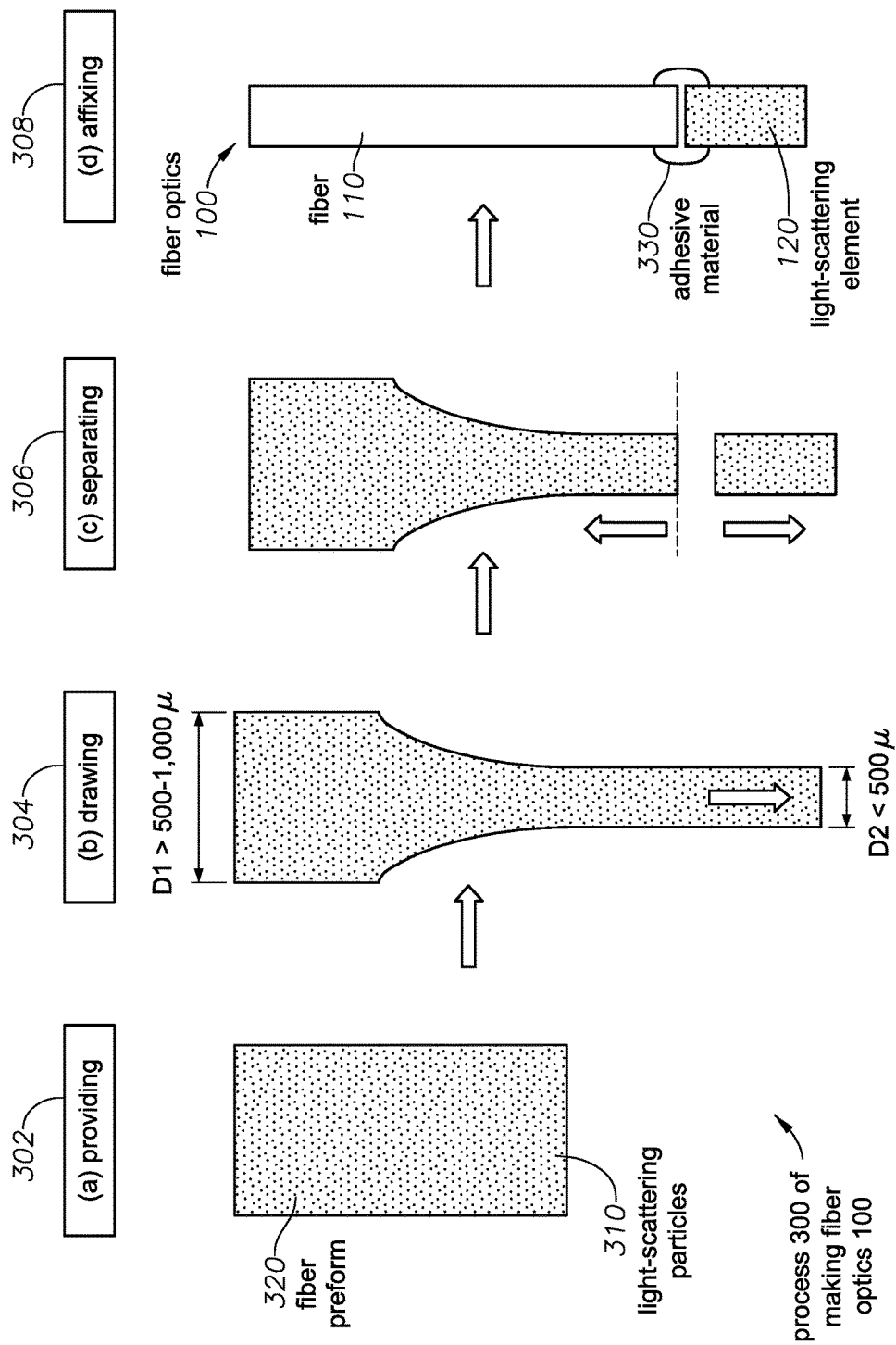
FIGS. 5A-D illustrate a process 300 of making the fiber optics 100.

FIG. 4 illustrates steps of a general process 200 to manufacture fiber optics 100. Step 202 can include providing the optical fiber 110, configured to receive illumination light at a proximal end from a light source.

Step 204 can include creating a light-scattering element 120 at a distal end of the optical fiber 110, configured to receive the illumination light from the optical fiber 110 at a proximal end and to emit the illumination light at a distal end in a wide angle. In some embodiments, the creating 204 step can involve creating a separate light-scattering element 120 and then affixing it to a distal end of the optical fiber 110, as in the embodiments of FIGS. 5, 7, 9, 11, 15 and 19. In other embodiments, the light-scattering element 120 can be created "at a distal end of the optical fiber" by creating it in a distal-end region of the optical fiber 110 itself, as in the embodiments of FIGS. 13 and 17, without necessarily affixing a separate element to the optical fiber 110. In these latter embodiments, the term "the light-scattering element is configured to receive the illumination light from the optical fiber at a proximal end" refers to the light propagating through the optical fiber 110 and entering into the light-scattering element 120 that was created at, or in, the distal-end region of the optical fiber 110.

FIGS. 5A-D illustrate the first of several methods and embodiments of how to practice this generic process, and the first of several embodiments of the fiber optics 100.

FIGS. 5A-D illustrate embodiments where the light-scattering element 120 includes light-scattering particles 310. In some designs, the light-scattering particles 310 can include $TiO_2$ particles or $Al_2O_3$ particles. The light-scattering particles 310 can have a diameter in the range of 100 nm-5μ. In some cases, their diameters can be in the 10 nm-50μ range. With diameters in these ranges, the light-scattering particles 310 can scatter the light effectively, enabling the light-scattering element 120 to emit the illumination light at its distal end in a wide angle.

The light-scattering element 120 can include a host material or matrix such as PMMA, silica, borosilicate, or a poly-carbonate polymer. The light-scattering particles 310 can be embedded, distributed, or mixed in with the host material or matrix.

The process 300 can include the following steps.

Step 302/FIG. 5A—(a) Providing a fiber preform 320 of a first diameter D1 that includes the host material, or matrix, and the light-scattering particles 310, embedded in the host material. The first diameter D1 of the preform 320 can be larger than 500μ, in other cases, larger than 1,000μ.

Step 304/FIG. 5B—(b) Drawing the fiber preform 320 to an extended length to reach a second diameter D2 that is smaller than the first diameter D1. The second diameter D2 can be less than 500μ. In some cases, D2 can be less than 150μ, in others, less than 50μ. Fibers with diameter of 125μ are widely used in optical communications, thus using fibers of similar diameter allows easy access to suitable starting fiber preforms and other materials as well as to fabrication technologies and tools.

Step 306/FIG. 5C—(c) Separating a portion of the drawn fiber preform 320 for use as the light-scattering element 120. FIG. 5C shows with the dashed line that the end of the drawn fiber preform 320, when it reached the design or target second diameter D2, can be broken, cut or otherwise separated from the rest of the preform 320.

Step 308/FIG. 5D—(d) Affixing the separated light-scattering element 120 to the distal end of the optical fiber 110 by bonding or by applying an adhesive material 330. Heat or chemical accelerators can be used as needed.

Figure 6:
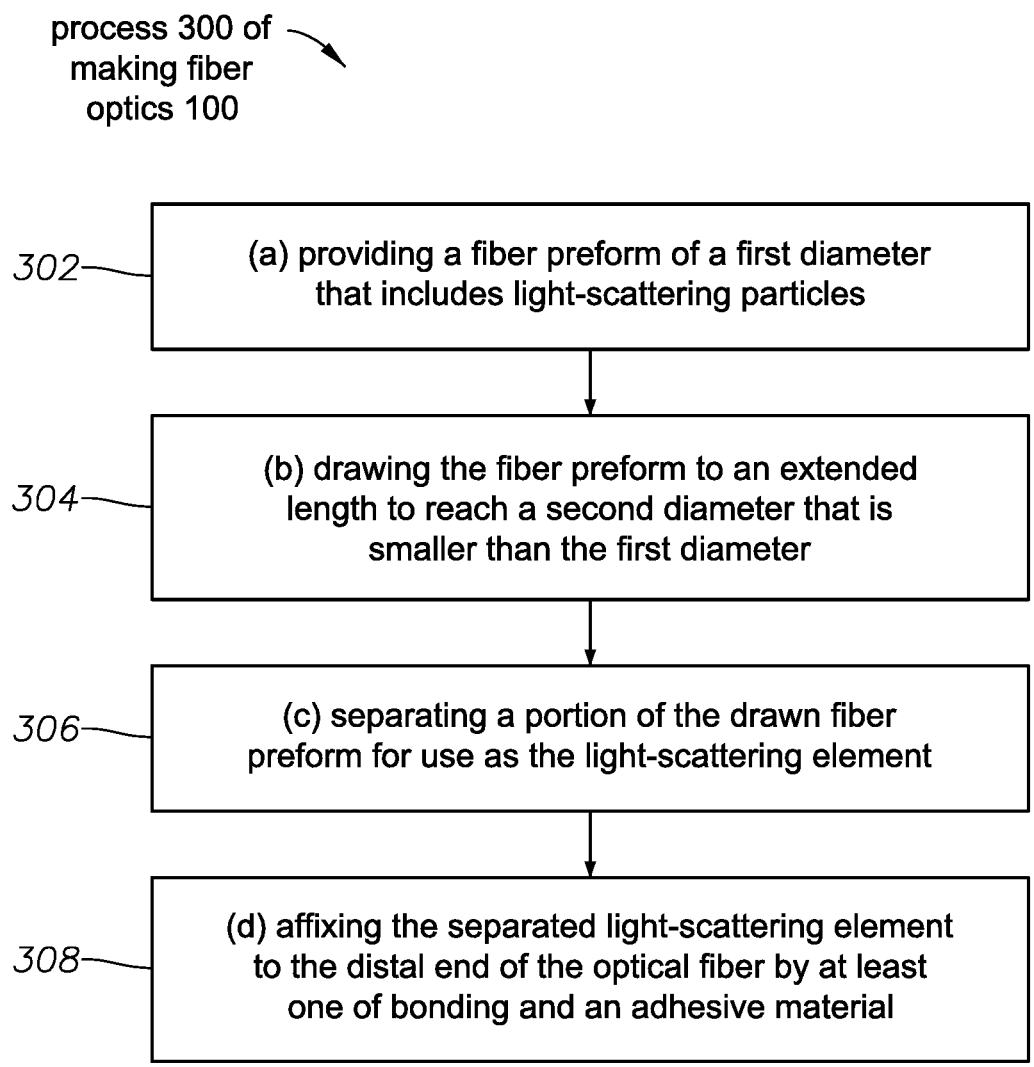
FIG. 6 illustrates the process 300 of making the fiber optics 100.

FIG. 6 illustrates the same steps 302-308 of the process 300 in a flowchart.

FIGS. 7A-B illustrate a process 400 for making the fiber optics 100. In some embodiments, this process 400 is designed to fabricate a light-scattering element 120 that includes a glass-ceramic micro-post 420, including at least one of a ceramic, a glass ceramic, an immiscible glass, a porous glass, opal glass, amorphous glass, an aerated glass, or a nanostructured glass. Here the phrase "glass-ceramic" broadly refers to micro-posts that can be made either of glass, or from ceramic, or from a glass-ceramic.

The process 400 can include the following steps.

Step 402/FIG. 7A—(a) Providing a glass-ceramic micro-post 420 comprising the glass-ceramic light-scattering element that includes a ceramic, a glass ceramic, an immiscible glass, a porous glass, opal glass, amorphous glass, an aerated glass, or a nanostructured glass. These embodiments do not necessarily utilize additional light-scattering elements like micro-spheres or light-scattering particles. Instead, they scatter the light by their own internal scatterers, such as the pores of the porous glass micro-post 420 embodiment.

Step 404/FIG. 7B—(b) Fusion-splicing the glass-ceramic micro-post 420 to the optical fiber 110. In some cases, fusion-splicing can be also referred to as fusing. The step 404 can further involve:

Step 406—(b1) Pulling an arc 430 between electrodes 440 across a gap formed by the optical fiber 110 and the glass-ceramic micro-post 420. The arc can heat up the fiber 110 as well as the glass-ceramic micro-post 420 to facilitate the fusion splicing.

Step 408—(b2) Maintaining the arc 430 for a time sufficiently long to make at least one of the facing surfaces of the optical fiber 110 and the micro-post 420 malleable or molten: in general, ready for the fusion-splicing, or fusing.

Step 410—(b3) Pushing together the facing, molten or malleable surfaces of the optical fiber 110 and the micro-post 420 after discontinuing the arc 430. Once the arc 430 is discontinued, the facing surfaces start cooling off and the re-hardening of the malleable or molten surface region, or regions, completes the fusion-splicing 404.

A distinguishing aspect of process 400 over process 300 is that in process 400 the light-scattering element 120 is attached to the fiber 110 with its own, molten material, without the use of additional materials, adhesive, or bonding agents. Such a design may reduce the backscatter and overheating effects at the affixation surface. This can be quite important, as overheating of the fiber optics 100 by the received illumination light heating the affixation surface between the fiber 110 and the light-scattering element 120 is a key factor limiting or even compromising the performance of today's fiber optics 100.

Figure 7D:
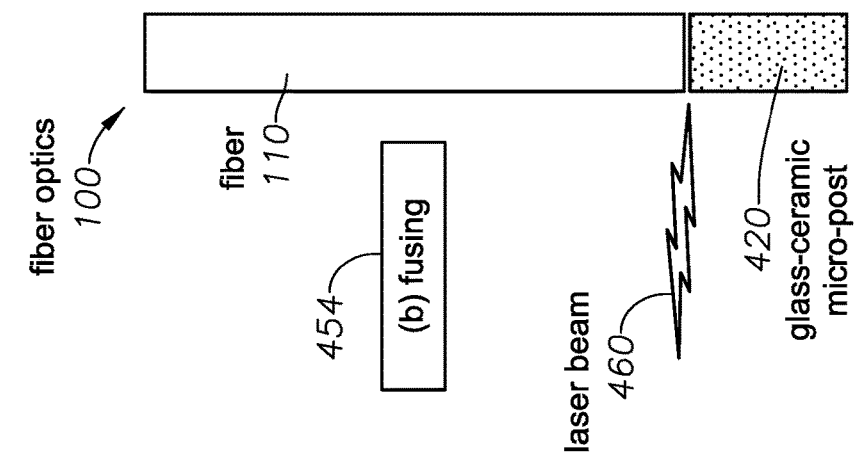
Figure 7C:
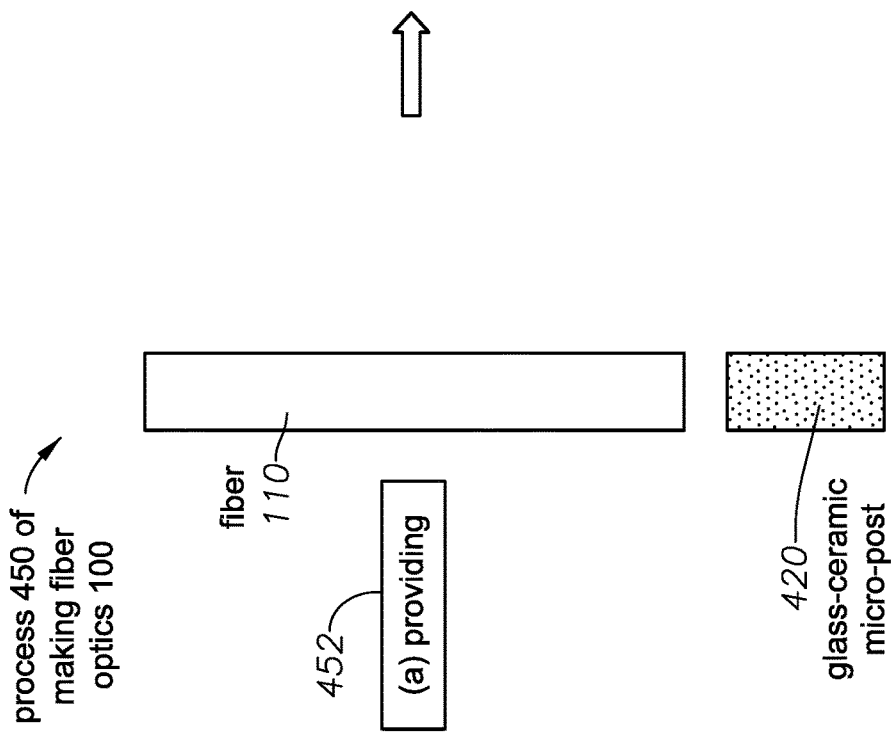

FIGS. 7C-D illustrate a related method 450. FIG. 7C illustrates step 452—(a) Providing a glass-ceramic micro-post 420 comprising the glass-ceramic light-scattering element that includes a ceramic, a glass ceramic, an immiscible glass, a porous glass, opal glass, amorphous glass, an aerated glass, or a nanostructured glass, in analogy to step 402.

Step 454/FIG. 7D—(b) Fusing the glass-ceramic micro-post 420 to the optical fiber 110 by applying a laser beam 460 to heat up at least one of the facing surfaces of the optical fiber 110 and the glass-ceramic micro-post 420. Visibly, step 454 is analogous to step 404, both heating up a portion of at least one of the optical fiber 110 and the glass-ceramic micro-post 420. Thus, steps 404 or 454 involve creating a malleable or molten surface region in at least one of the optical fiber 110 and the glass-ceramic micro-post 420, so that they can be fused, or fusion-spliced, together subsequently.

Figure 8A:
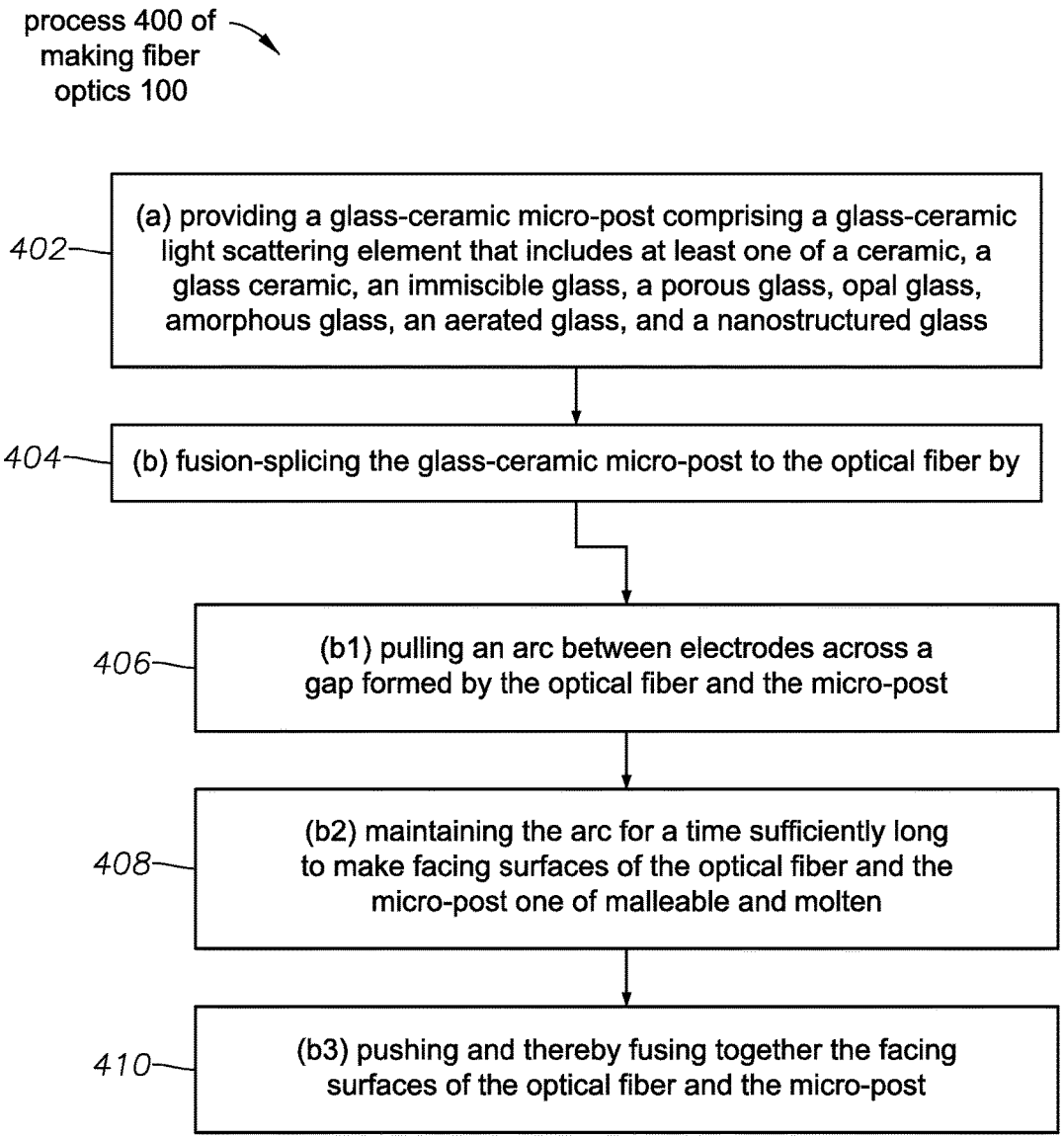
FIGS. 8A-B illustrate the processes 400/450 of making the fiber optics 100.

FIG. 8A is a flowchart of the steps 402-410 of the process 400.

Figure 8B:
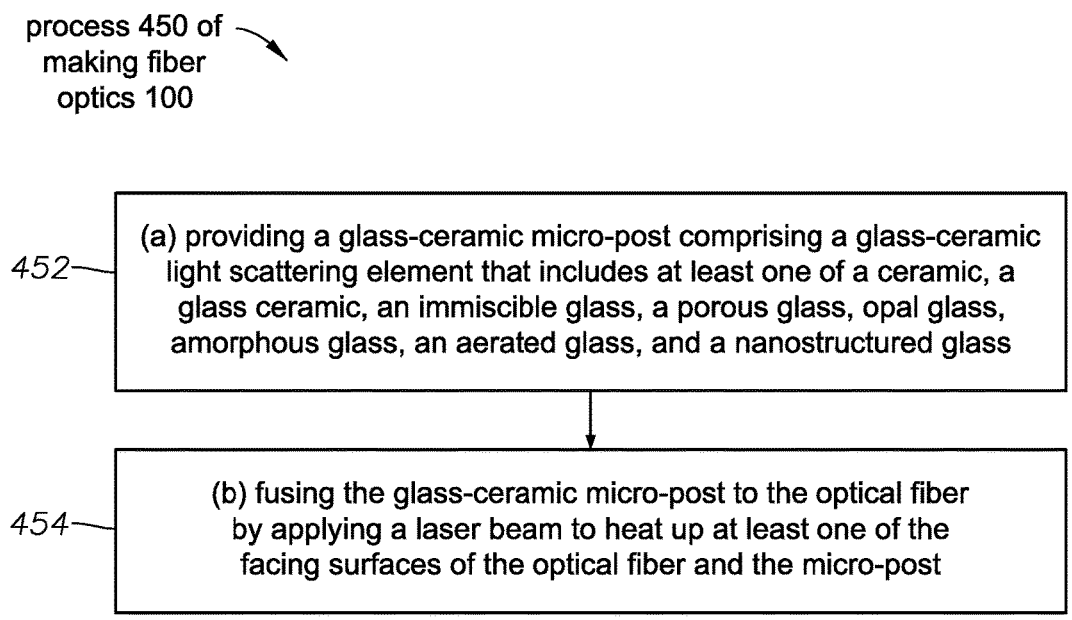

FIG. 8B is a flowchart of the steps 452-454 of the process 450.

FIGS. 9A-D illustrate a process 500 for making embodiments of the fiber optics 100. One shared characteristic of these embodiments is that the light-scattering element 120 includes glass microspheres 510. A diameter of the glass microspheres 510 can be in the range of 0.5-10μ. With diameters in this range, the glass microspheres 510 can scatter the light effectively, enabling the light-scattering element 120 to emit the illumination light at its distal end in a wide angle.

Steps of the process 500 can include the following steps.

Step 502/FIG. 9A—(a) Providing glass microspheres 510 in a polymer matrix liquid bath 520. Typically, the bath 520 is heated to an elevated temperature so that the polymer of the bath 520 is malleable, deformable, or even a melt, or fluid. The glass microspheres 510 can be distributed or dispersed about evenly in the bath 520 with stirring, or mechanical, or other means.

Step 504/FIG. 9B—(b) Dipping the optical fiber 110 into the polymer matrix liquid bath 520. The optical fiber 110 can also be heated in embodiments where this brings further advantages.

Step 506/FIG. 9C—(c) Extracting the optical fiber 110 from the polymer matrix liquid bath 520. As the fiber 110 is pulled out, or extracted from the bath 520, an amount of the malleable but viscous polymer liquid, or polymer melt 520 can stick to the fiber 110. From this polymer material, stuck onto the distal tip of the extracted fiber 110, the surface tension of the polymer liquid 520 can form a glass ball 530 that includes the glass microspheres 510, embedded in the polymer melt 520. The distal end, or the distal tip of the fiber 110 that includes the sidewalls of the fiber 110, can be roughened for better mechanical connection between the fiber 110 and the glass ball 530.

Step 508/FIG. 9D—(d) Sintering the glass ball 530 via heating by a heat source. The sintering 508 can reduce, and in some cases entirely eliminate, the polymer melt content of the glass ball 530, leaving behind only a densely packed assembly of the glass microspheres 510, sintered together by the heat. In some embodiments, a diameter of the glass ball 530 ball can be in the range of 10μ-1,000μ. In some embodiments, a diameter of the glass ball 530 ball can be in the range of 10μ-100μ.

In the glass ball 530, the glass microspheres 510 can be sintered together to create a refractive index gradient between the glass microspheres and air-voids between the glass microspheres. These refractive index gradients and the air-voids can play an important role in scattering the light.

Figure 10:
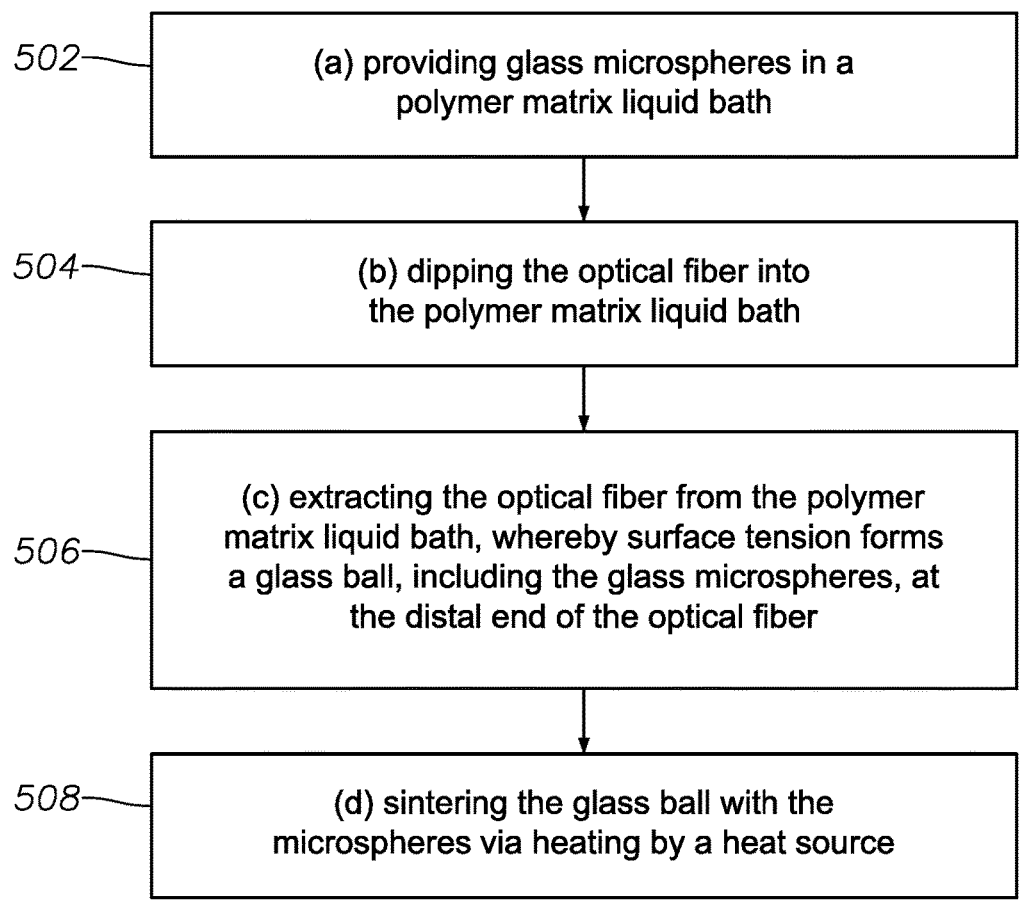
FIG. 10 illustrates the process 500 of making the fiber optics 100.

FIG. 10 illustrates the step 502-508 of the process 500 in a flowchart.

Figures 11A, 11B, 11C:
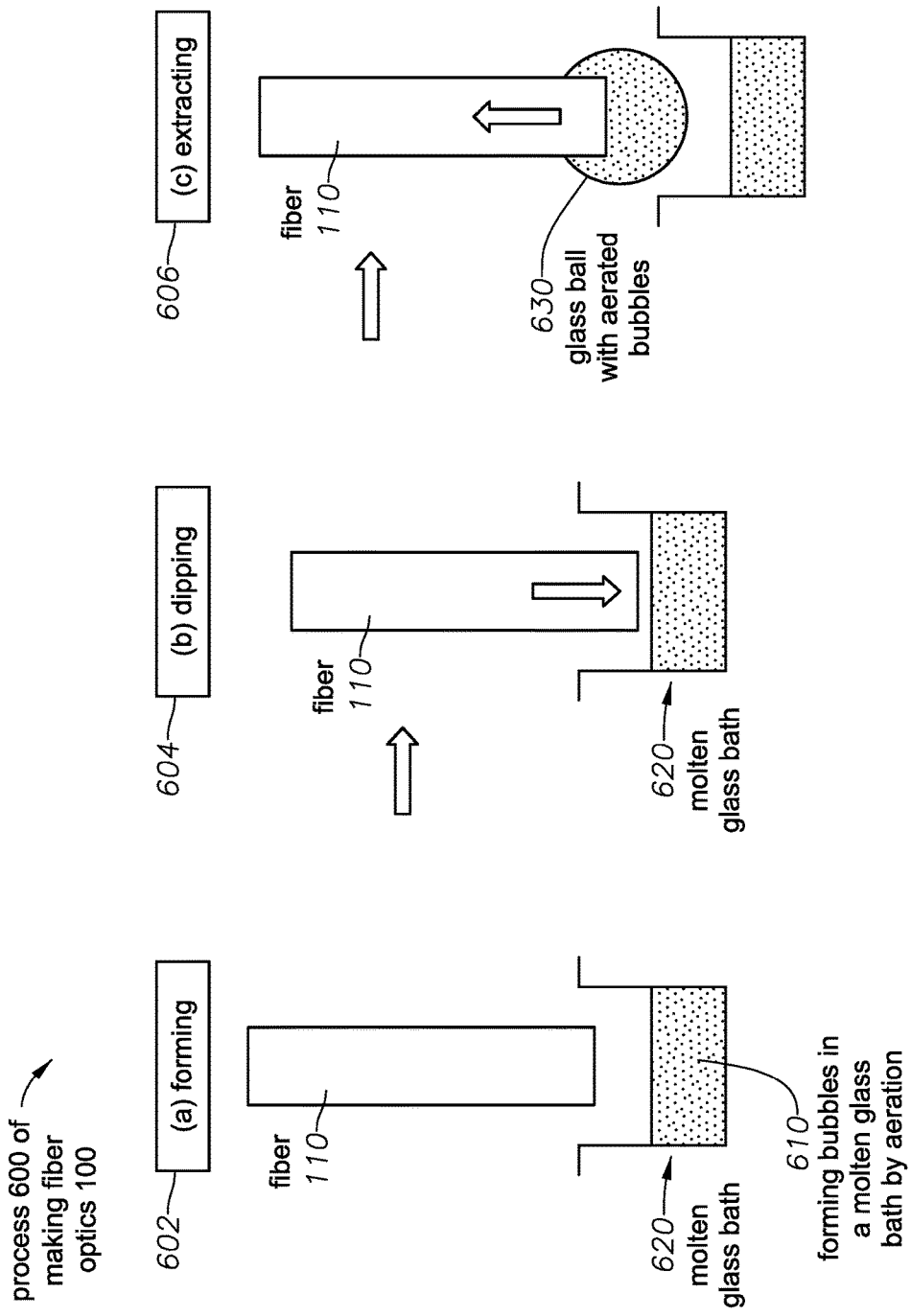
FIGS. 11A-C illustrate a process 600 of making the fiber optics 100.

FIGS. 11A-C illustrate a process 600 of fabricating the fiber optics 100. In this embodiment, the light scattering is driven by bubbles formed inside a glass ball element when it is in a molten state. The bubbles can be formed by aeration, that is, by guiding bubbles into the molten glass by a pump, for example.

The process 600 can include the following steps.

Step 602/FIG. 11A—(a) Forming micro-bubbles 610 in a molten glass bath 620 by aeration. The glass in the bath can be melted by heating it above its melting temperature.

Step 604/FIG. 11B—(b) Dipping the optical fiber 110 into the molten glass bath 620.

Step 606/FIG. 11C—(c) Extracting the optical fiber 110 from the molten glass bath 620. As the fiber 110 is pulled out from the molten glass bath 620, the surface tension of the melt forms the glass ball 630 with aerated bubbles, at the distal end of the optical fiber 110.

Figure 12:
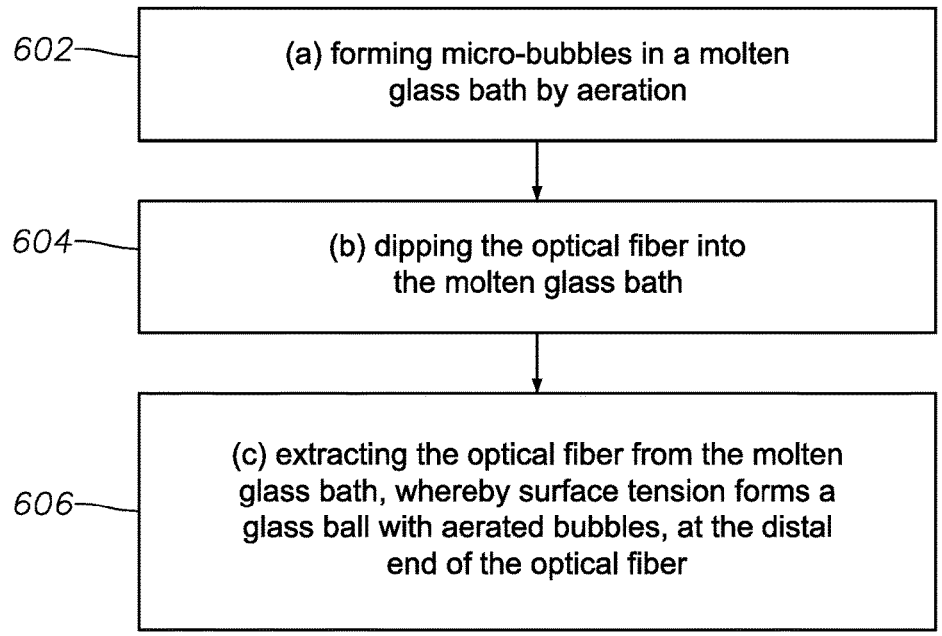
FIG. 12 illustrates the process 600 of making the fiber optics 100.

FIG. 12 illustrates the steps 602-606 of the process 600 in a flowchart.

Figure 13A:
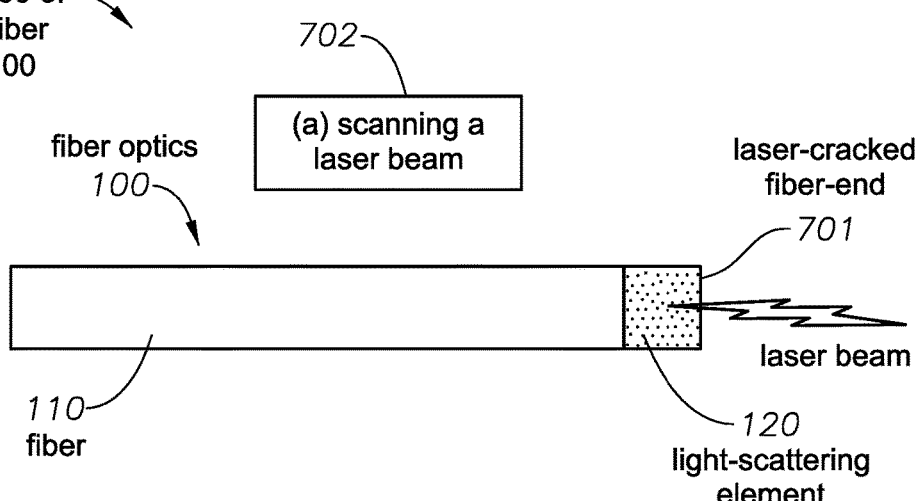
FIGS. 13A-B illustrate a process 700 of making the fiber optics 100.
Figure 13B:
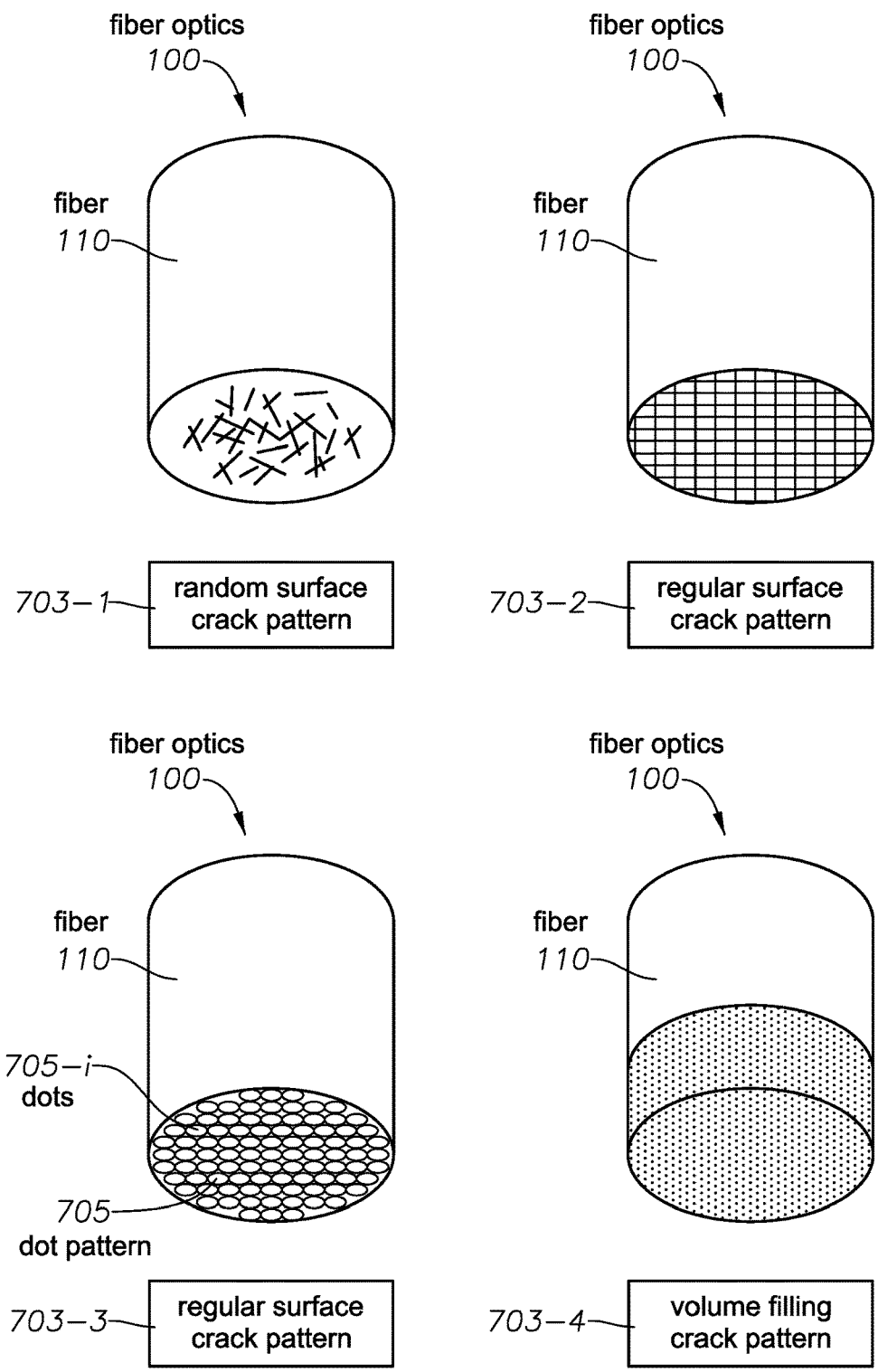

FIGS. 13A-B illustrate a process 700 to fabricate the fiber optics 100. In this process 700, the light scattering is driven by cracks, formed in a laser-cracked fiber-end region 701 of the optical fiber 110. As such, this process is somewhat different from some of the previous processes, as no light-scattering element 120 is formed separately and then subsequently affixed to the optical fiber 110. Instead, the creating the light-scattering element 120 involves forming the light-scattering element 120 in the distal-end region of the optical fiber 110.

The process 700 can include the following steps.

Step 702/FIG. 13A—(a) Scanning a laser beam across the distal end of the optical fiber 110 to cause the formation of a laser-cracked fiber-end 701 with a crack pattern 703, having air pockets, in the distal end of the fiber 110.

FIG. 13B illustrates that the crack pattern 703 can be a random surface crack pattern 703-1 on the distal end of the optical fiber, a regular surface crack pattern 703-2 or 703-3 on the distal end of the optical fiber, or a volume filling crack pattern 703-4 in a region at the distal end of the optical fiber.

For example, the regular pattern 703-3 can be a repeating regular array of dots, or bubbles, 705-$i$ with a diameter D in the 10-500μ range, in some cases in the 50-100μ range. These dots/bubbles can be separated by 1-100μ, in some cases by 1-5μ. These dots 705-$i$ can form a dot-pattern 705. The dots 705-$i$ can be created by sequentially directing, or scanning, a pulsed laser beam to an array, or pattern, of points, where the beam either causes local heating that directly cracks the optical fiber 110, or the beam forms bubbles that expand and eventually crack the optical fiber 110. In either case, scanning the pulsed laser beam can create a light-scattering element 120 in the distal-end region of the optical fiber 110 that includes a laser-patterned, or laser-cracked, fiber-end 701 with a refractive index pattern caused by the pattern of dots, or bubbles.

Figure 14:
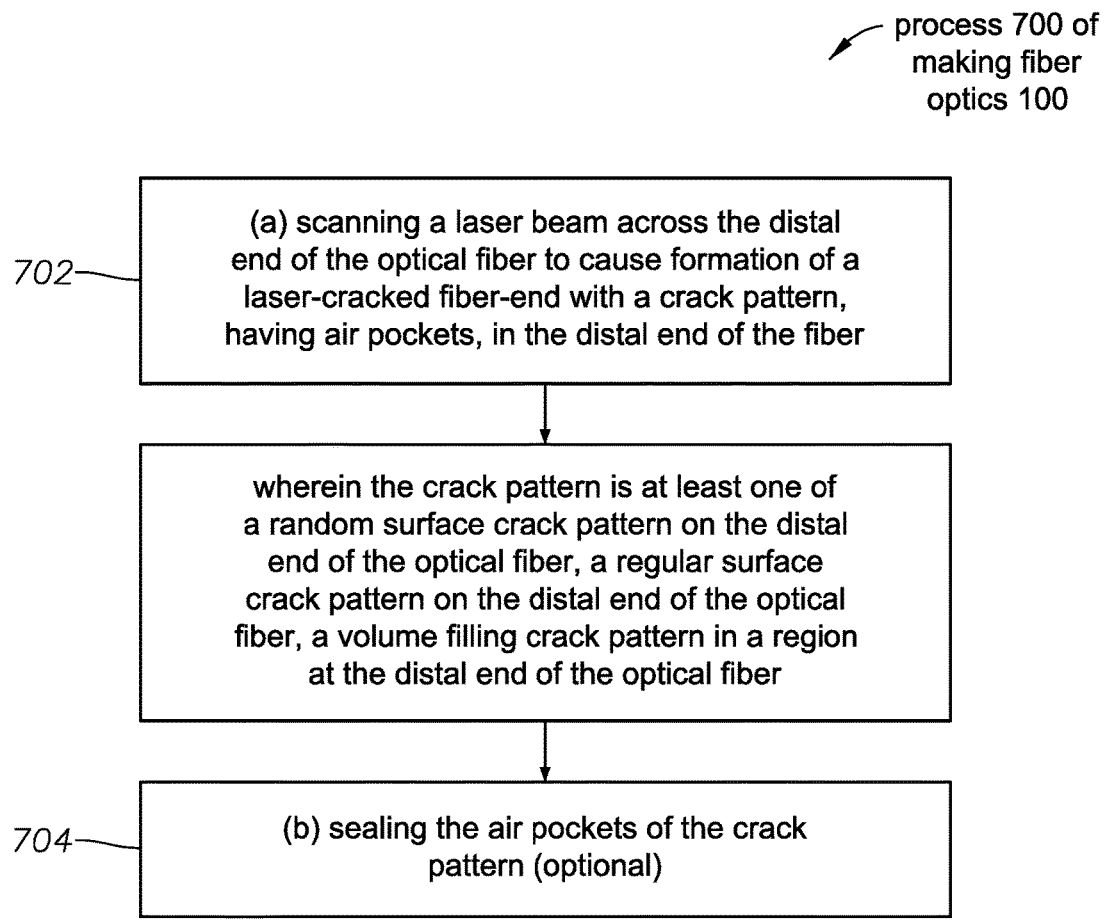
FIG. 14 illustrates the process 700 of making the fiber optics 100.
Figure 15:
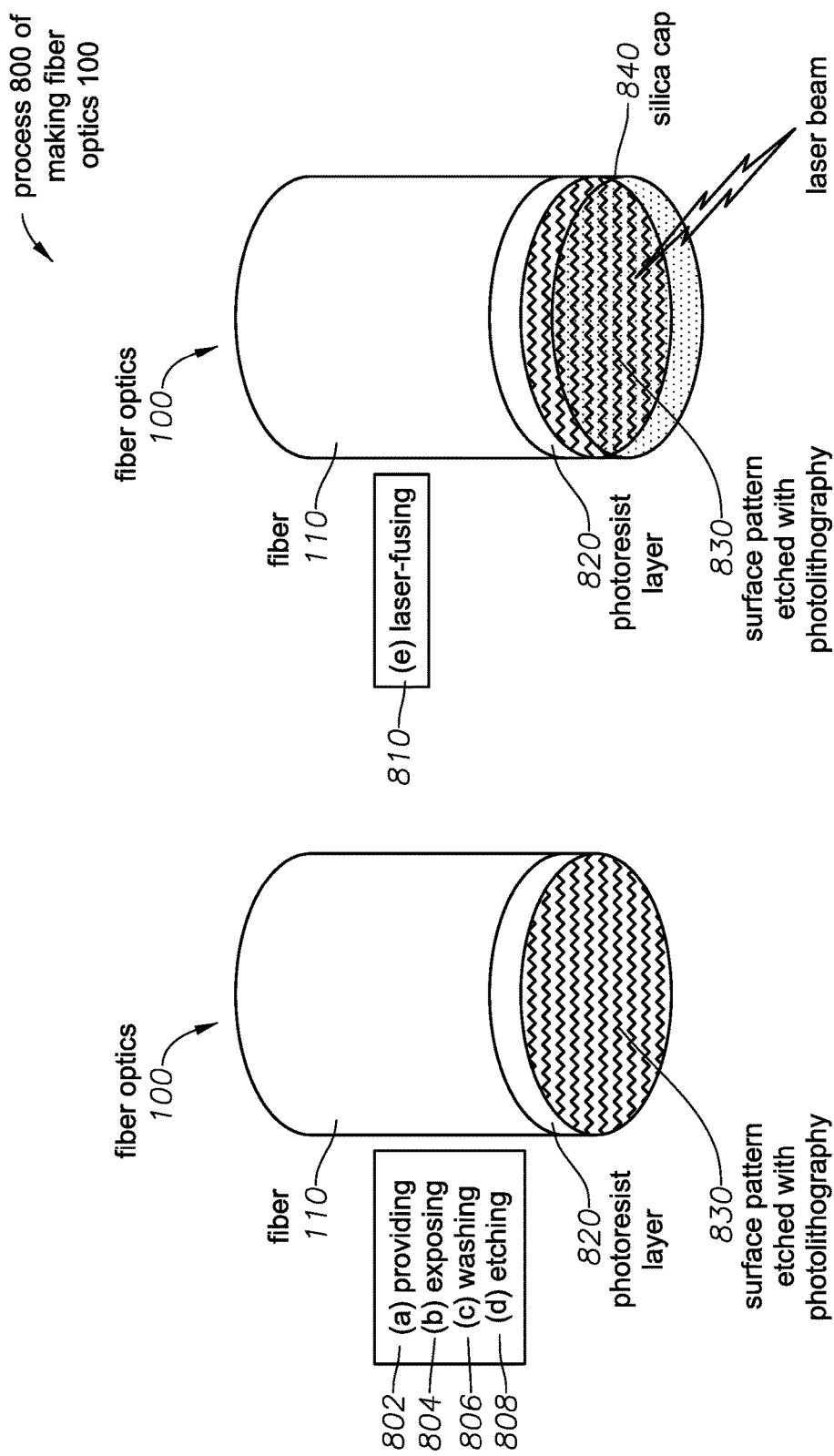
FIGS. 15A-B illustrate a process 800 of making the fiber optics 100.

FIG. 14 illustrates the process 700 in a flowchart. This chart includes the optional additional step 704—(b) Sealing the air pockets of the crack pattern 703. The air pockets often form in the cracks and contribute or even dominate the light scattering. Accordingly, it is important to preserve these air pockets even when the fiber optics 100 is inserted into ophthalmic tissue with a high liquid content. Such biological environments are often modeled with a "balanced salt solution", or BSS. Therefore, process 700 can include the additional step to seal the crack pattern 703 either by depositing a sealing layer such as an adhesive, a silica, or a coat, or by scanning the laser beam across the surface at a lower power, or lower power density so that it only melts the glass surface, thereby sealing the cracks.

FIGS. 15A-B illustrate a process 800 for making the fiber optics 100. With process 800 the light-scattering element 120 is formed by a photolithographic process in the following steps.

Step 802/FIG. 15A—(a) Providing a photoresist layer 820 on the distal end of the optical fiber 110. This photoresist layer 820 can be deposited, evaporated, or affixed to the optical fiber 110 in a variety of ways.

Step 804/FIG. 15A—(b) Exposing the photoresist layer 820 to a speckle light pattern. The speckle light pattern can be provided by shining a light or laser light through a diffuser, a diffuse medium, an amorphous medium, a grating, crossed optical patterns, or through other suitable means. The speckle light is held fixed for a period of time sufficient to induce the photochemical processes needed to affect the proper exposure in the photoresist layer 820.

Step 806/FIG. 15A—(c) Washing off unexposed photoresist. This step reveals a pattern formed by the exposed photoresist, enabling the next, photolithographic step of etching.

Step 808/FIG. 15A—(d) Etching the distal end of the optical fiber 110 in hydrofluoric acid, or in a comparably strong acid, to impart a surface pattern 830 with air-pockets to the etched distal end of the optical fiber 110. The etched surface pattern 830 will serve as the light-scattering element 120 in these embodiments.

The surface pattern 830 can be completely random, or pseudo-random. In some cases, a more regular pattern may be preferred, in which case instead of using a speckle light pattern in step 804, a regular light pattern may be used. The photolithographic steps 802-808 are very well known and therefore are not illustrated in individual Figures.

Step 810/FIG. 15B—(e) Laser-fusing a silica end-cap 840 to the distal end of the optical fiber 110 to seal the air-pockets. As before, since in some embodiments the air getting into the etched surface pattern 830 plays an important role in scattering the illumination light, it can be useful to seal the air pockets of the surface pattern 830, so that they are protected in a balanced salt solution (BSS).

Figure 16:
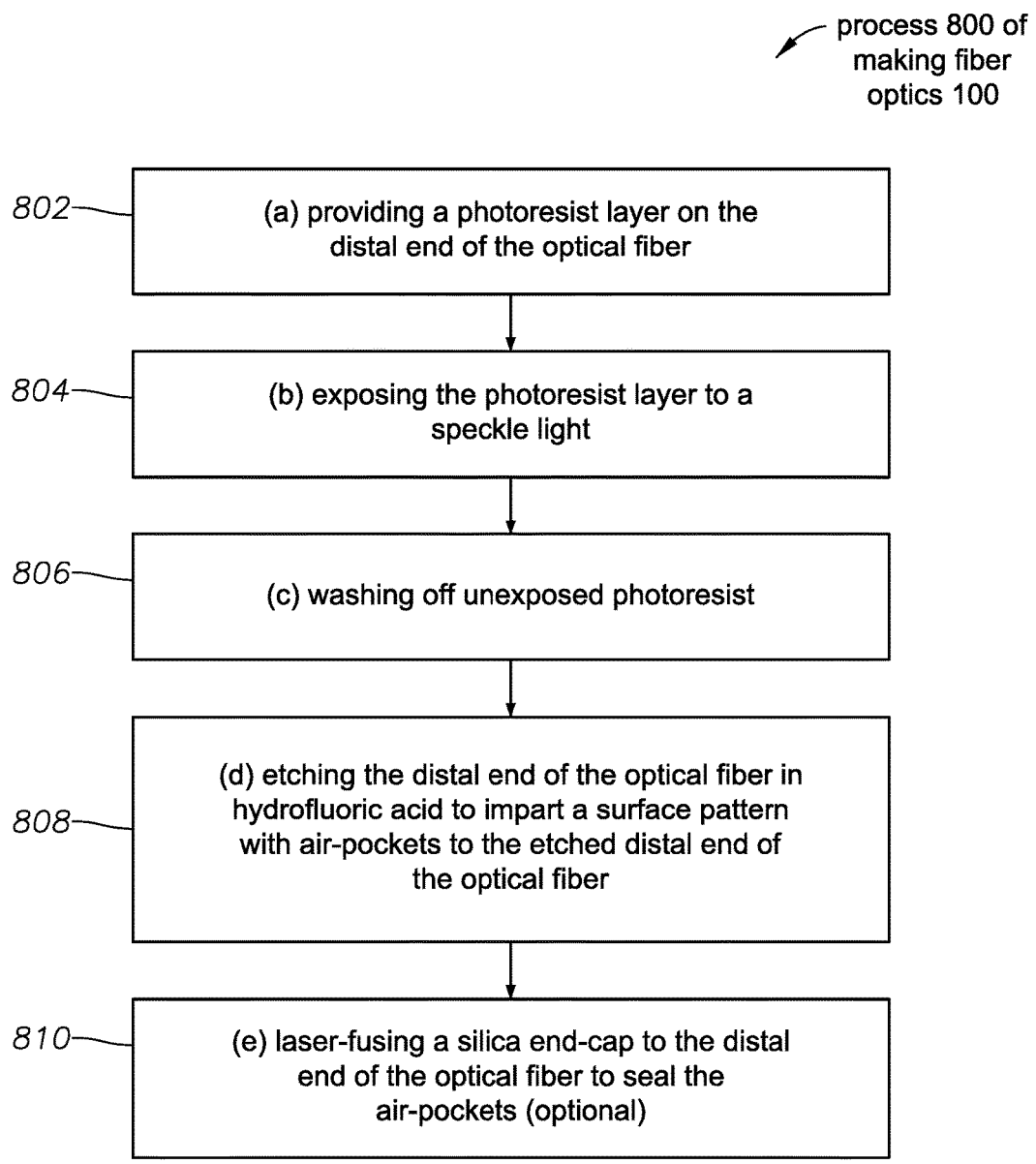
FIG. 16 illustrates the process 800 of making the fiber optics 100.

FIG. 16 illustrates the steps 802-810 of the process 800 in a flowchart.

In some embodiments, the process 800 can be performed as a batch process. This can involve aligning and arranging hundreds or even thousands of fibers 110 in a tight bundle, or batch, held together either by a machine-member, or by a manufacturing sheath, and then performing the photolithographic ("recording") steps 802-808 and the laser-fusing step 810 on the bundle, in essence simultaneously on all the fibers. Such batch processing can increase the yield of the fabrication process 800 dramatically. An analogous batch processing will be illustrated in FIG. 17D.

FIGS. 17A-D illustrate a process 900 for making the fiber optics 100.

Step 902/FIG. 17A—(a) Providing a hard tool 910 with a nanostructured tool surface relief pattern 920. The hard tool 910 can be made of steel, or other hard material, considerably harder than the glass material of the fiber 110.

The tool surface relief pattern 920 can be formed by several different methods. One of them is to use a photolithographic process to transfer a speckle laser light pattern onto the surface of the hard tool with the help of a photoresist layer that was exposed to the speckle light and subsequently etched.

Step 904/FIG. 17B—(b) Pressing the tool surface relief pattern 920 of the hard tool 910 onto the distal end of the optical fiber 110 to form a fiber surface relief pattern 930 on the distal end of the optical fiber 110 by molding or hot stamping. In this process step the hard tool 910 can be warmed up to heat the distal end of the fiber 110 when pressed onto it, or the distal end of the fiber 110 can be directly heated. In either case, the heating will make the fiber 110 more malleable and deformable and thus helps the transfer of the tool surface relief pattern 920 onto the distal end of the fiber to form the fiber surface relief pattern 930. The heating can be performed by applying a heat source or a radiation source. Once the formation of the fiber surface relief pattern 930 is completed, the fiber 110 can be removed or separated from the hard tool 910.

Step 906/FIG. 17C—(c) Laser-fusing a silica end-cap 940 to the distal end of the optical fiber 110 to seal air pockets of the fiber surface relief pattern 930. This step 906 can be optional.

Figure 17D:
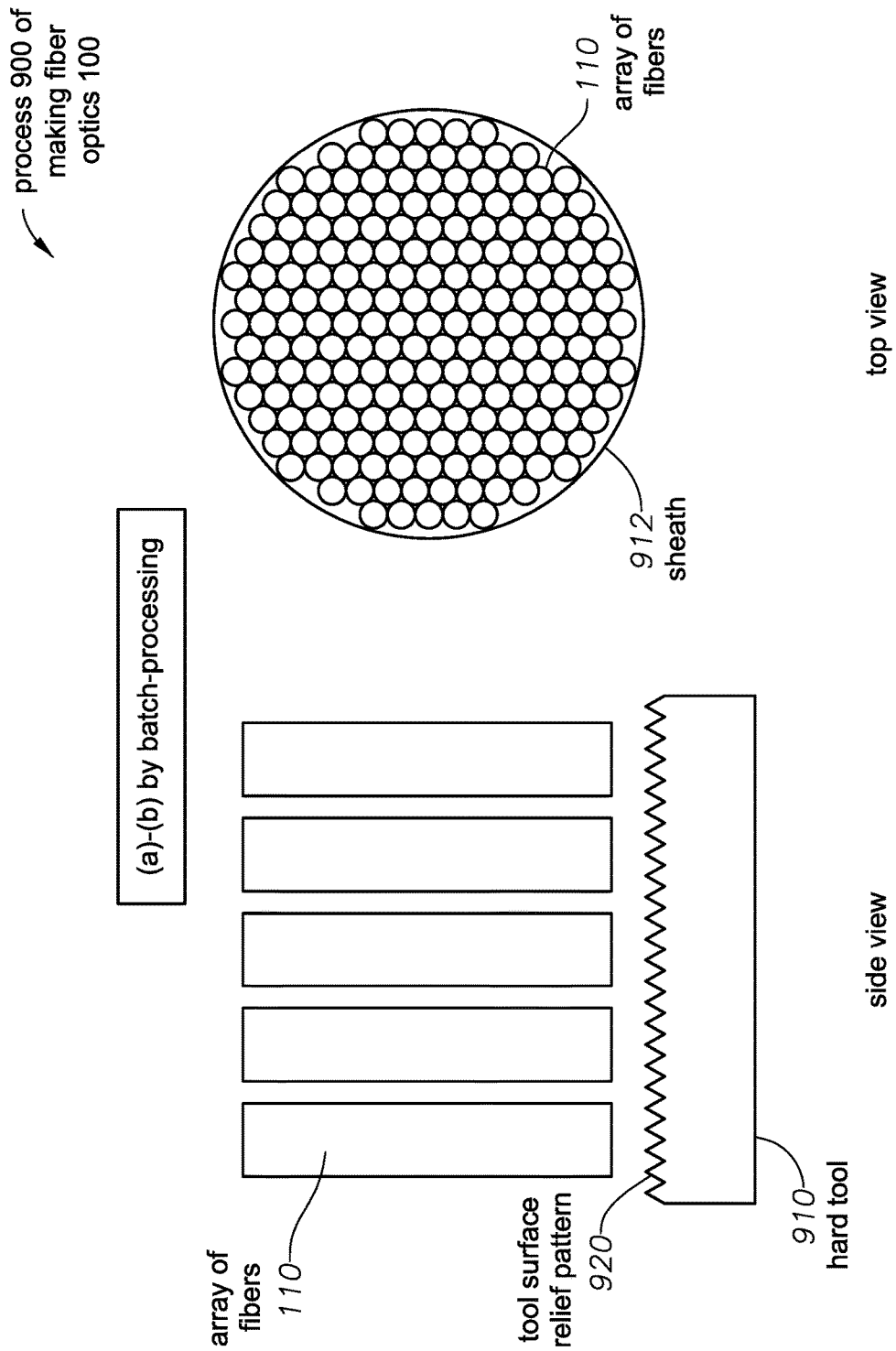

FIG. 17D illustrates that the providing step 902 and the pressing step 904 can be performed as a batch process. As also described in relation to the process 800, this batch process can involve aligning and arranging hundreds or even thousands of fibers 110 in a tight bundle, array, or batch, held together either my a machine-member, or by a manufacturing sheath 912, and then performing the steps 902-904 on the bundle, in essence simultaneously on all the fibers 110. Such batch processing can increase the yield of the fabrication process 900 dramatically.

Figure 18:
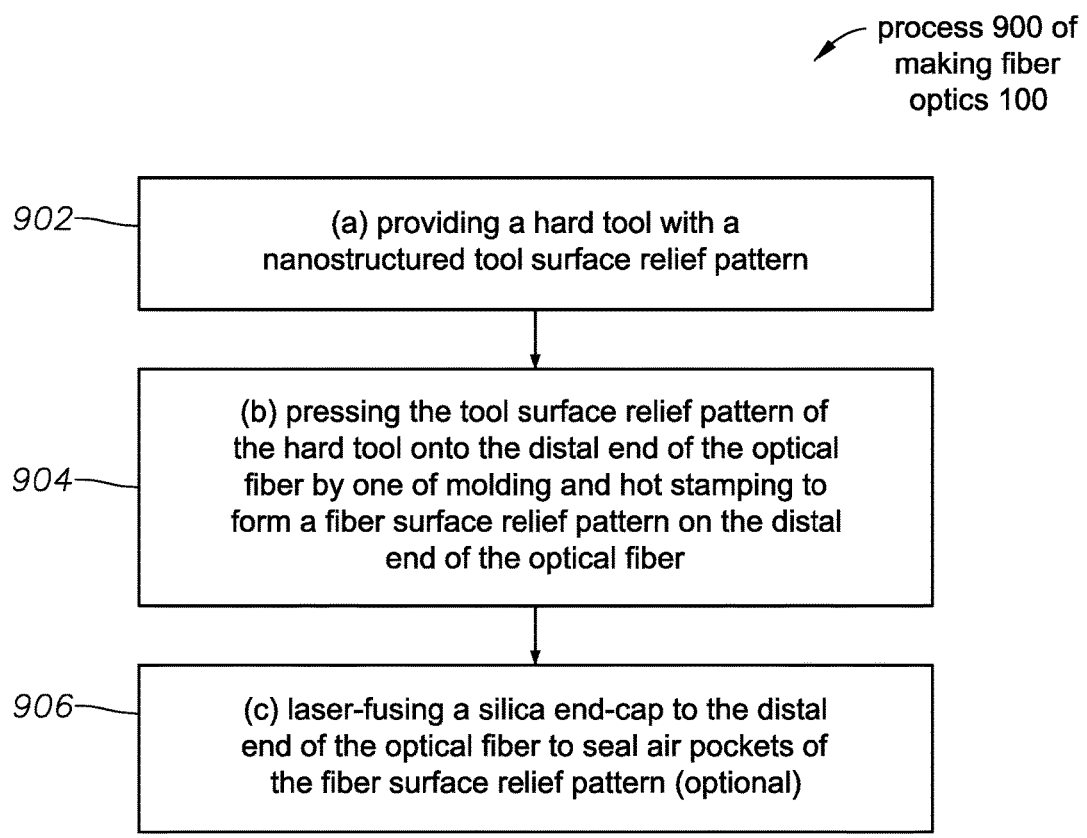
FIG. 18 illustrates the process 900 of making the fiber optics 100.

FIG. 18 illustrates the process 900 in a flowchart.

FIGS. 19A-F illustrate a process 1000 for making the fiber optics 100. The process 1000 involves forming a cured patterned adhesive 1070, UV-cured at the distal end of the fiber 100 by the following steps.

Step 1002/FIG. 19A—(a) Providing a hard tool 1020 with a nanostructured tool surface relief pattern 1030. The hard tool 1020 can include steel or other hard materials.

Step 1004/FIG. 19B—(b) Pressing the tool surface relief pattern 1030 of the hard tool 1020 onto a first side of a UV-transparent plastic wafer 1040 by molding or hot stamping to form a wafer surface relief pattern 1050 on the UV-transparent plastic wafer 1040.

Step 1006/FIG. 19C—(c) Depositing a UV-curable adhesive 1060 on the wafer surface relief pattern 1050 on the UV-transparent wafer 1040.

Step 1008/FIG. 19D—(d) Pressing the distal end of the optical fiber 110 against the wafer surface relief pattern 1050 with the UV-curable adhesive 1060.

Step 1010/FIG. 19D—(e) Curing the UV-curable adhesive 1060 by radiating a UV beam through the UV-transparent wafer 1040 from a second side of the UV-transparent wafer 1040 opposite the first side of the UV-transparent wafer. This curing step solidifies the UV-curable adhesive 1050, and thus the wafer surface relief pattern 1050 imparts a solidified, or cured, relief pattern onto the UV-curable adhesive 1060.

Step 1012/FIG. 19E—(f) Lifting the optical fiber 110 with a lifted cured patterned adhesive 1070 from the UV-transparent wafer 1040. The curing creates a bond between a portion of the UV-curable adhesive 1050 and the optical fiber 110 that is strong enough to lift a portion 1070 of the UV-curable adhesive 1060 away from the UV-transparent wafer 1040 and from the rest of the UV-curable adhesive 1060.

As was the case of processes 800, and 900, process 1000 can be executed as a batch process, thus accelerating the process 1000 and increasing its yield dramatically. Beyond the specifically discussed cases of processes 800-1000, all previously described processes 200-700 can be also performed as a batch process.

Figure 20:
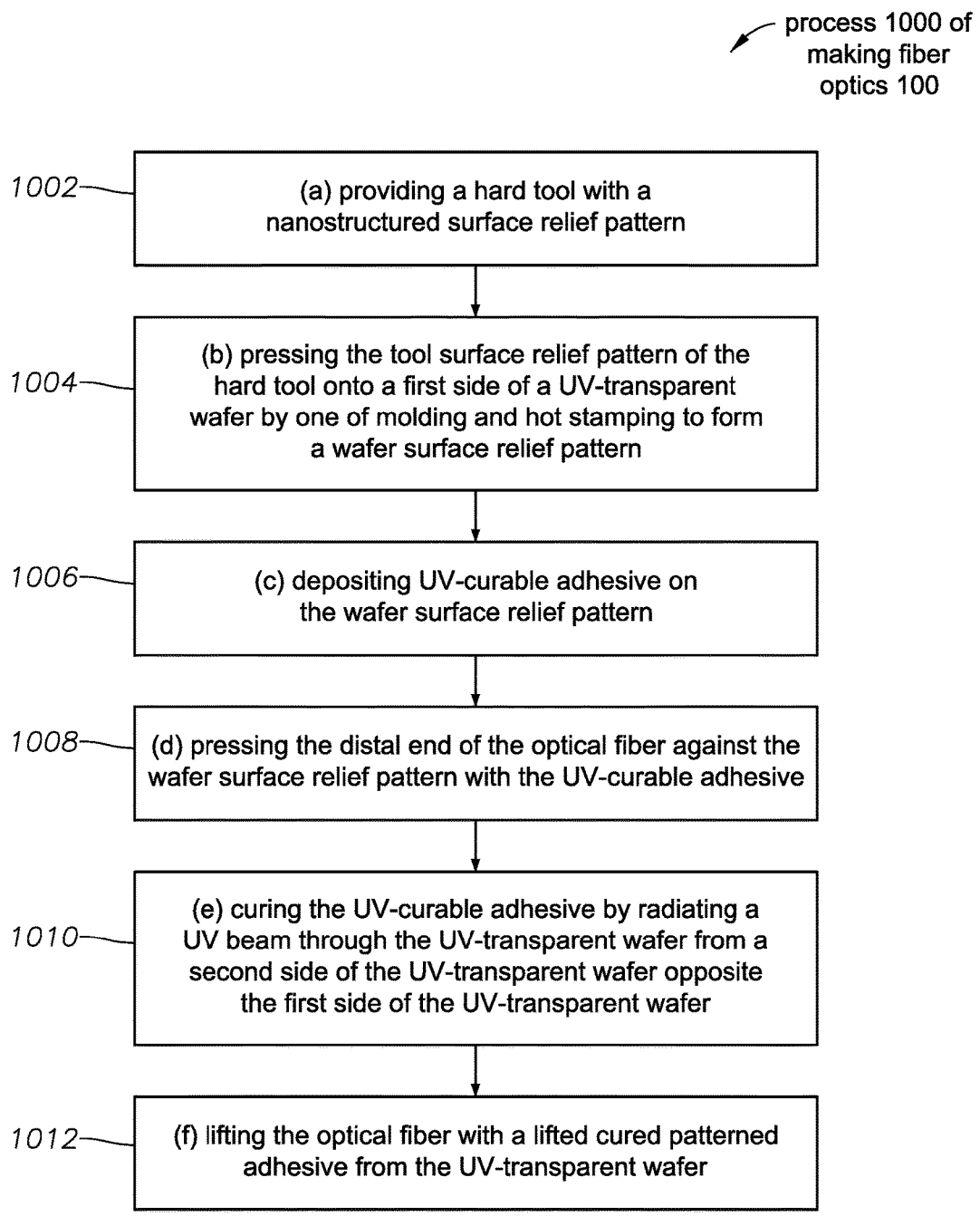
FIG. 20 illustrates the process 1000 of making the fiber optics 100.

FIG. 20 illustrates the steps 1002-1012 of the process 1000 in a flowchart.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

The invention claimed is:

1. An illumination fiber optics, comprising:
   an optical fiber, configured to receive illumination light at a proximal end from a light source; and
   a light-scattering element, at a distal end of the optical fiber, configured to receive the illumination light from the optical fiber at a proximal end of the light-scattering element and to emit the illumination light at a distal end of the light-scattering element in a wide angle;
   wherein the light-scattering element is created by:
   (a) providing glass microspheres in a polymer matrix liquid bath;
   (b) dipping the optical fiber into the polymer matrix liquid bath;
   (c) extracting the optical fiber from the polymer matrix liquid bath, whereby surface tension forms a glass ball, including the glass microspheres, at the distal end of the optical fiber; and
   (d) sintering the glass ball with the microspheres via heating by a heat source, wherein sintering the glass ball reduces a polymer melt content of the glass ball.

2. The fiber optics of claim 1, wherein:
   an outer diameter of the fiber optics is less than 500 microns.

3. The fiber optics of claim 1, wherein:
   an outer diameter of the fiber optics is less than 150 microns.

4. The fiber optics of claim 1, wherein:
   an outer diameter of the fiber optics is less than 50 microns.

5. The fiber optics of claim 1, wherein:
   an outer diameter of the fiber optics is less than 50 microns at a distal end; and
   an outer diameter of the fiber optics is greater than 50 microns at a proximal end.

6. The fiber optics of claim 1, wherein:
   the optical fiber and the light-scattering element are manufactured without using a manufacturing jacket.

7. The fiber optics of claim 1, wherein:
   the fiber optics is attached to an ophthalmic surgical device at an accommodation notch in an aligned manner, configured to emit the illumination light at the distal end of the light-scattering element to serve as an illumination light for a surgical procedure performed by the surgical device.

8. The fiber optics of claim 7, wherein:
   the ophthalmic surgical device has an outer diameter thinner than 23 gauge; and
   the attached fiber optics does not increase one of a form factor and an overall diameter of the ophthalmic surgical device.

9. The fiber optics of claim 7, wherein:
   the surgical device is one of an articulated laser probe, an illuminating chandelier, a trocar cannula, a balanced salt solution (BSS) infusion line, a nanofiber endo-illuminator, a forceps, a phaco-surgical device, a retinal-surgical device, and a vitreous-cutter.

10. The fiber optics of claim 1, wherein:
    the fiber optics is centrally embedded in an ophthalmic surgical device along an optical axis of the ophthalmic surgical device, wherein
    an outer diameter of the ophthalmic surgical device is thinner than 40 gauge.

11. The fiber optics of claim 1, wherein:
    the wide angle is characterized in that an illumination intensity in air at 60 degrees off an optical axis of the fiber optics is greater than 2% of the illumination intensity in air at 0 degrees, along the optical axis of the fiber optics.

12. The fiber optics of claim 1, wherein:
    the wide angle is characterized in that an illumination intensity in air at 30 degrees off an optical axis of the fiber optics is greater than 50% of the illumination intensity in air at 0 degrees, along the optical axis of the fiber optics.

13. The fiber optics of claim 1, wherein:
    a diameter of the glass microspheres is in the range of $0.5\mu$-$10\mu$; and
    the light-scattering element is a glass ball, including the microspheres, with a diameter in the range of $10\mu$-$1,000\mu$.

14. The fiber optics of claim 13, wherein:
    the light-scattering element is a glass ball, including the microspheres, with a diameter in the range of $10\mu$-$100\mu$.

15. The fiber optics of claim 1, wherein:
    the glass microspheres are sintered together to create a refractive index gradient between the glass microspheres and air-voids between the glass microspheres.

16. An illumination fiber optics for an ophthalmic device, prepared by a process comprising the steps of:
    providing an optical fiber, configured to receive illumination light at a proximal end from a light source; and
    creating a light-scattering element at a distal end of the optical fiber, configured to receive the illumination light from the optical fiber at a proximal end of the light-scattering element and to emit the illumination light at a distal end of the light-scattering element in a wide angle,
    wherein creating the light-scattering element comprises:
    (a) providing glass microspheres in a polymer matrix liquid bath;
    (b) dipping the optical fiber into the polymer matrix liquid bath;

(c) extracting the optical fiber from the polymer matrix liquid bath, whereby surface tension forms a glass ball, including the glass microspheres, at the distal end of the optical fiber; and
(d) sintering the glass ball with the microspheres via heating by a heat source, wherein sintering the glass ball reduces a polymer melt content of the glass ball.

* * * * *

UNITED STATES PATENT AND TRADEMARK OFFICE
CERTIFICATE OF CORRECTION

PATENT NO. : 10,295,718 B2
APPLICATION NO. : 14/973939
DATED : May 21, 2019
INVENTOR(S) : Alireza Mirsepassi et al.

Page 1 of 1

It is certified that error appears in the above-identified patent and that said Letters Patent is hereby corrected as shown below:

On the Title Page

(73) Assignee: reads as Novaris AG, Basel (CH) when it should read Novartis AG, Basel (CH).

Signed and Sealed this
Eleventh Day of February, 2020

Andrei Iancu
*Director of the United States Patent and Trademark Office*